United States Patent
Jin et al.

(10) Patent No.: US 12,416,035 B2
(45) Date of Patent: Sep. 16, 2025

(54) RECOMBINANT PARTICLE PROTEIN PRODUCT SUITABLE FOR INDUSTRIAL PRODUCTION AND PREPARATION METHOD THEREFOR

(71) Applicants: Yantai Patronus Biotech Co., Ltd., Yantai (CN); Guangzhou Patronus Biotech Co., Ltd., Guangdong (CN)

(72) Inventors: Jing Jin, Guangzhou (CN); Yu Zhou, Guangzhou (CN)

(73) Assignees: Yantai Patronus Biotech Co., Ltd., Yantai (CN); Guangzhou Patronus Biotech Co., Ltd., Guangzhou (CN)

( * ) Notice: Subject to any disclaimer, the term of this patent is extended or adjusted under 35 U.S.C. 154(b) by 0 days.

(21) Appl. No.: 18/743,724

(22) Filed: Jun. 14, 2024

(65) Prior Publication Data

US 2024/0344101 A1 Oct. 17, 2024

Related U.S. Application Data

(63) Continuation of application No. PCT/CN2022/116392, filed on Sep. 1, 2022.

(30) Foreign Application Priority Data

Dec. 17, 2021 (CN) .............................. 202111553371

(51) Int. Cl.
| | |
|---|---|
| C12P 21/00 | (2006.01) |
| C07K 1/18 | (2006.01) |
| C07K 1/20 | (2006.01) |

(52) U.S. Cl.
CPC ................ C12P 21/00 (2013.01); C07K 1/18 (2013.01); C07K 1/20 (2013.01)

(58) Field of Classification Search
CPC .............. C12P 21/00; C07K 1/18; C07K 1/20
See application file for complete search history.

(56) References Cited

FOREIGN PATENT DOCUMENTS

| | | | | |
|---|---|---|---|---|
| CN | 104098700 | | 10/2014 | |
| CN | 109134620 | | 1/2019 | |
| CN | 109134621 | | 1/2019 | |
| CN | 109966483 | | 7/2019 | |
| CN | 111991556 | | 11/2020 | |
| CN | 111991556 A | * | 11/2020 | ............. A61K 39/12 |
| CN | 112089831 | | 12/2020 | |
| CN | 114395015 | | 4/2022 | |
| WO | WO-2021210984 A1 | * | 10/2021 | ............. A61K 39/12 |
| WO | WO 2022088953 | | 5/2022 | |

OTHER PUBLICATIONS

Ng, M.Y.T. et al. "Heat treatment of unclarified *Escherichia coli* homogenate improved the recovery efficiency of recombinant hepatitis B core antigen". Journal of Virology Methods, vol. 137 (2006), pp. 134-139. (Year: 2006).*
Eiggenreich, B. et al. "High pressure homogenization is a key unit operation in inclusion body processing". Journal of Biotechnology, vol. 324, Supplement (2020), p. 100022. (Year: 2020).*
Ho, C.W. et al. "Comparative evaluation of different cell disruption methods for the release of recombinant Hepatitis B Core Antigen from *Escherichia coli*." Biotechnology and Bioprocess Engineering, vol. 13 (2008), pp. 577-583. (Year: 2008).*
De Bernardez Clark, E. et al. "Inhibition of Aggregation side reactions during in vitro protein folding". Methods in Enzymology, vol. 309 (1999), pp. 217-236. (Year: 1999).*
Hirsch, J. et al. "*E. coli* production process yields stable dengue 1 virus-sized particles (VSPs)." Vaccine, vol. 38 (2020), pp. 3305-3312. (Year: 2020).*
Handbooks of GE Healthcare, Ion Exchange Chromatography & Chromatofocusing, Principles and Methods (2018), downloaded on Sep. 14, 2024, from URL [www.med.unc.edu/pharm/sondeklab/wp-content/uploads/sites/868/2018/10/Ion-exchange.pdf] (Year: 2018).*
Cai, H. et al. "One-step heating strategy for efficient solubilization of recombinant spider silk protein from inclusion bodies." BMC Biotechnology, vol. 20 (2020), p. 37. (Year: 2020).*
Bruun, T. U.J. et al. "Engineering a Rugged Nanoscaffold to Enhance Plug-and-Display Vaccination".ACS Nano, vol. 12 (2018), pp. 8855-8866. (Year: 2018).*
Beneš, M.J .et al. "Methacrylate-based chromatographic media". Journal of Separation Science, vol. 28 (2005), pp. 1855-1875. ( Year: 2005).*
Fractogel Data Sheet pdf, downloaded from internet on Sep. 24, 2024 (Year: 2024).*
Shi, W. et al. "Preparation of a novel hydrophobic interaction chromatography with higher selectivity by introducing spatial recognition". Journal of Chemical Technology and Biotechnology, vol. 95 (2020), pp. 2195-2207 (Year: 2020).*
Kubo, M. and Nishi, A. "Improved method for pro-urokinase refolding with inclusion body from recombinant *Escherichia coli*". Journal of Fermentation and Bioengineering, vol. 80, No. 6 (1995), pp. 622-624. (Year: 1995).*
Rosa da Silva, C.M. et al. "Association of high pressure and alkaline condition for solubilization of inclusion bodies and refolding of the NS1 protein from zika virus". BMC Biotechnology, vol. 18 (2018), p. 78. (Year: 2018).*

(Continued)

*Primary Examiner* — Neil P Hammell
*Assistant Examiner* — Alexander Geraldine Dace Denito
(74) *Attorney, Agent, or Firm* — Fish & Richardson P.C.

(57) ABSTRACT

The present invention relates to a recombinant particle protein suitable for industrial production and a preparation method therefor. The product is prepared by the following method: transfecting a host cell with a plasmid vector comprising a sequence encoding the recombinant particle protein for expression in the cell, harvesting and disrupting the bacterial cells, heating, incubating with urea and sodium chloride, and performing chromatography. The particle size of the product is uniform, and the batch-to-batch consistency in particle size is good. The product prepared by the method can reduce the cost of large-scale industrial mass production, the method is simple to operate, and the product has low impurity residue and a good safety profile.

17 Claims, 14 Drawing Sheets
Specification includes a Sequence Listing.

(56) References Cited

OTHER PUBLICATIONS

Bruun et al., "Engineering a Rugged Nanoscaffold to Enhance Plug-and-Display Vaccination," ACS Nano, Sep. 2018, available online Jul. 20, 2018, 12(9):8855-8866.

International Search Report and Written Opinion in International Appln. No. PCT/CN2022/116392, mailed on Dec. 1, 2022, 19 pages (with English translation).

Li et al., "An RBD virus-like particle vaccine for SARS-CoV-2 induces cross-variant antibody responses in mice and macaques," Signal Transduct Target Ther, Apr. 2023, 8(1), 173, 20 pages (including Supplementary Materials).

Ng et al., "Heat treatment of unclarified Escherichia coli homogenate improved the recovery efficiency of recombinant hepatitis B core antigen," J Virol Methods, Oct. 2006, available online Jul. 24, 2006, 137(1):134-139.

Rahikainen et al., "Overcoming Symmetry Mismatch in Vaccine Nanoassembly through Spontaneous Amidation," Angew. Chem. Int. Ed., 60(1):321-330, 18 pages (including the supplemental material).

Xie et al., "The Purification Procedure for the Recombinant HBcAg Virus-like Particle Easy to Generate Aggregation," China Biotechnology, Dec. 31, 2020, 40(5):40-47 (with English Abstract).

\* cited by examiner

Results of size exclusion chromatography for a sample treated with 6 M urea for 1 h Results of size exclusion chromatography for a sample treated with 6 M urea for 17 h Results of size exclusion chromatography for a sample treated with 4 M urea for 1 h Results of size exclusion chromatography for a sample treated with 4 M urea for 17 h SDS-PAGE detection results of size exclusion elution peaks after treatment with 4 M urea Results of size exclusion chromatography for a sample treated with 1 M urea for 1 h Results of size exclusion chromatography for a sample treated with 1 M urea for 17 h SDS-PAGE detection results of size exclusion elution peaks after treatment with 1 M urea Results of size exclusion chromatography for a sample without urea treatment Results of size exclusion chromatography for a sample soaked with 8 M urea for 1 h Results of size exclusion chromatography for a sample soaked with 8 M urea for 16 h a. SDS-PAGE for chromatographic peaks after treatment with 50 mM sodium chloride b. SDS-PAGE for chromatographic peaks after treatment with 100\150\200 mM sodium chloride

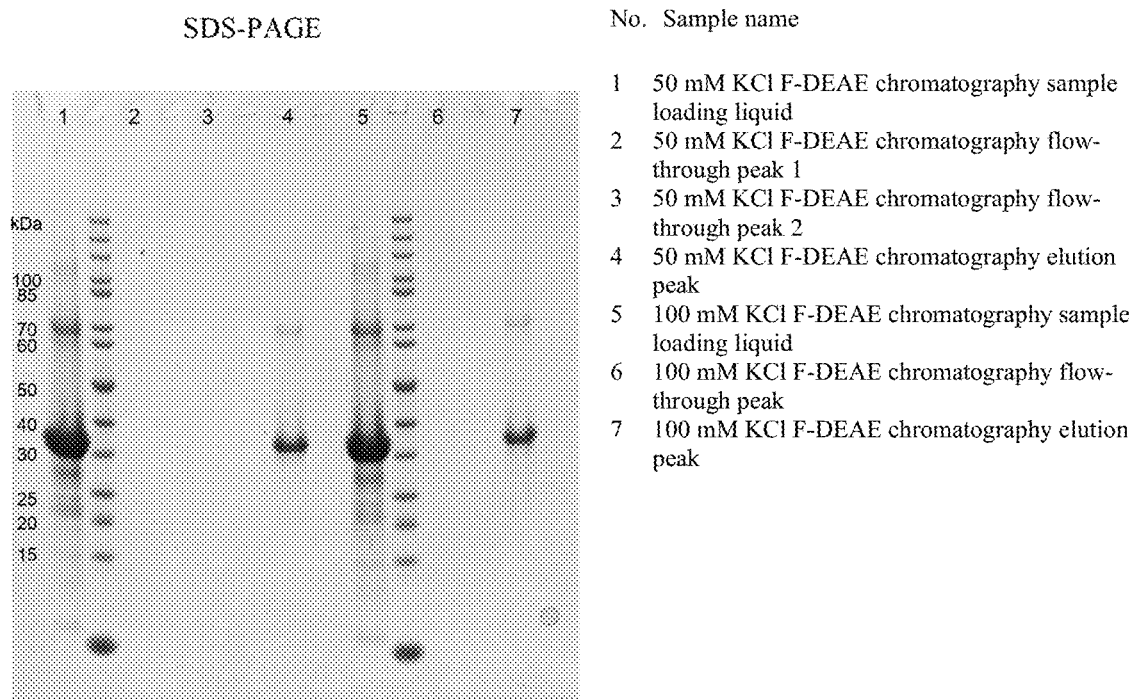
FIG. 14(a)
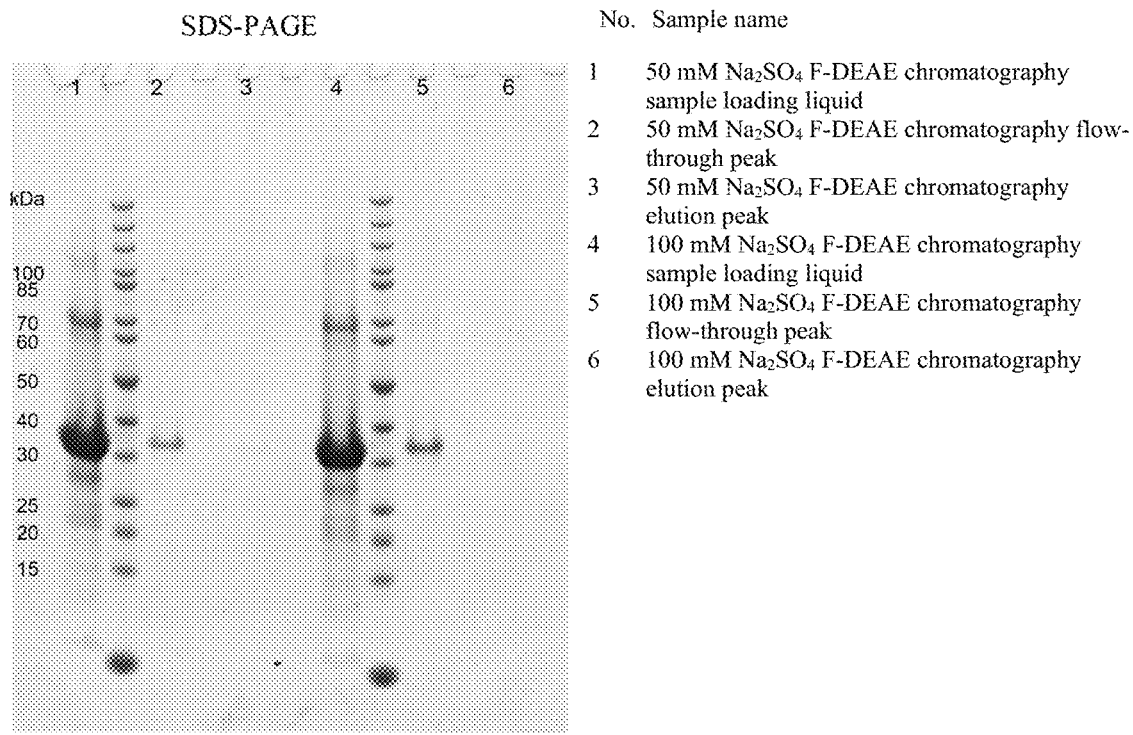
FIG. 14(b)
FIG. 14

RECOMBINANT PARTICLE PROTEIN PRODUCT SUITABLE FOR INDUSTRIAL PRODUCTION AND PREPARATION METHOD THEREFOR

CROSS-REFERENCE TO RELATED APPLICATIONS

This application is a bypass continuation and claims priority to PCT/CN2022/116392, filed on Sep. 1, 2022, which claims priority to Chinese Application No. 202111553371.9, filed on Dec. 17, 2021. The content of the foregoing applications are incorporated herein by reference in their entirety for all purposes.

SEQUENCE LISTING

This application contains a Sequence Listing that has been submitted electronically as an XML file named "58421-0002001.XML." The XML file, created on Jun. 13, 2024, is 2,258 bytes in size. The material in the XML file is hereby incorporated by reference in its entirety.

TECHNICAL FIELD

The present invention relates to the technical field of bio-pharmaceuticals, and particularly to a recombinant particle protein product and a production and preparation method therefor.

BACKGROUND

Recombinant particle protein products can be prepared by various preparation methods within the scope of common technical knowledge (such as salt precipitation, density gradient centrifugation, filtration, chromatography, dialysis, and the like). However, during the industrial production and preparation of particle proteins, there are still challenges such as difficulty in formation, low preparation purity, high industrial production cost, and the like. Therefore, developing a high-efficiency, stable, simple, convenient and low-cost recombinant particle protein product and a preparation method therefor suitable for industrial production is still a problem that needs to be addressed in the art.

SUMMARY

The present invention provides a recombinant particle protein product suitable for industrial production, wherein the amino acid sequence of the protein is set forth in SEQ ID NO: 1.

```
>SEQ ID NO: 1
DSATHIKFSKRDEDGKELAGATMELRDSSGKTISTWISDGQVKDFYLYPG

KYTFVETAAPDGYEVATAITFTVNEQGQVTVNGKATKGDAHIGGSGGSGG

SGGSMKMEELFKKHKIVAVLRANSVEEAKKKALAVFLGGVHLIEITFTVP

DADTVIKELSFLKEMGAIIGAGTVTSVEQARKAVESGAEFIVSPHLDEEI

SQFAKEKGVFYMPGVMTPTELVKAMKLGHTILKLFPGEVVGPQFVKAMK

GPFPNVKFVPTGGVNLDNVCEWFKAGVLAVGVGSALVKGTPVEVAEKAK

AFVEKIRGCTE
```

The present invention provides a recombinant particle protein product suitable for industrial production, wherein the amino acid sequence of the protein is set forth in SEQ ID NO: 1, and the recombinant particle protein product is prepared by the following steps:
(1) transfecting a host cell with a plasmid vector comprising a sequence encoding the recombinant particle protein for expression in the cell; (2) harvesting the bacterial cells, and disrupting the same through high-pressure homogenization; (3) a. adjusting the pH of a high-pressure homogenization supernatant to 7.0-9.0, heating the supernatant at 80-100° C. for more than 15 min, returning to room temperature, then performing centrifugation, discarding a pellet, collecting a supernatant, and adding a dilution buffer to adjust the pH value to 7.0-8.0; and b. heating the solution at 50-70° C. for 5-30 min, immediately performing centrifugation, discarding a supernatant, collecting a pellet, and resuspending the pellet in a resuspension buffer at pH 7.0-11.0; (4) adding urea and sodium chloride, wherein the urea is at a concentration of 6-8 M; and (5) performing anion exchange chromatography and hydrophobic chromatography.

The present invention provides a recombinant particle protein product suitable for industrial production, wherein the amino acid sequence of the protein is set forth in SEQ ID NO: 1, and the recombinant particle protein product is prepared by the following steps:
(1) transfecting a host cell with a plasmid vector comprising a sequence encoding the recombinant particle protein for expression in the cell; (2) harvesting the bacterial cells, and disrupting the same through high-pressure homogenization; (3) a. adjusting the pH of a high-pressure homogenization supernatant to 8.0-10.0, heating the supernatant at 80-95° C. for 15-80 min, returning to room temperature, then performing centrifugation, discarding a pellet, collecting a supernatant, and adding a dilution buffer to adjust the pH value to 7.0-8.0; and b. heating the solution at 50-65° C. for 5-20 min, immediately performing centrifugation, discarding a supernatant, collecting a pellet, and resuspending the pellet in a resuspension buffer at pH 7.0-11.0; (4) adding urea and sodium chloride; and (5) performing anion exchange chromatography and hydrophobic chromatography.

The present invention provides a recombinant particle protein product suitable for industrial production, wherein the amino acid sequence of the protein is set forth in SEQ ID NO: 1, and the recombinant particle protein product is prepared by the following steps:
(1) transfecting a host cell with a plasmid vector comprising a sequence encoding the recombinant particle protein for expression in the cell; (2) harvesting the bacterial cells, and disrupting the same through high-pressure homogenization; (3) a. adjusting the pH of a high-pressure homogenization supernatant to 7.0-8.0, incubating the supernatant at 4-25° C. for more than 15 min, returning to room temperature, then performing centrifugation, discarding a pellet, collecting a supernatant, and adding a dilution buffer to adjust the pH value to 7.0-8.0; and b. heating the solution at 50-70° C. for 5-30 min, immediately performing centrifugation, discarding a supernatant, collecting a pellet, and resuspending the pellet in a resuspension buffer at pH 7.0-11.0; (4) adding urea and sodium chloride; and (5) performing anion exchange chromatography and hydrophobic chromatography.

The present invention provides a recombinant particle protein product suitable for industrial production, wherein the amino acid sequence of the protein is set forth in SEQ ID NO: 1, and the recombinant particle protein product is prepared by the following steps:
(1) transfecting a host cell with a plasmid vector comprising a sequence encoding the recombinant particle protein for expression in the cell; (2) harvesting the bacterial cells, and disrupting the same through high-pressure homogenization; (3) a. adjusting the pH of a high-pressure homogenization supernatant to 9.0; incubating the supernatant at 4-95° C. for more than 15 min; preferably, heating and incubating the supernatant at 60-90° C. for 15-60 min, more preferably, heating and incubating the supernatant at 80-90° C. for 15-45 min; then, after returning to room temperature, performing centrifugation, discarding a pellet, collecting a supernatant, and adding a dilution buffer to adjust the pH value to 7.0-8.0; and b. heating and incubating the solution at 50-70° C. for 5-30 min, immediately performing centrifugation, discarding a supernatant, collecting a pellet, and resuspending the pellet in a resuspension buffer at pH 7.0-11.0; (4) adding urea and sodium chloride; and (5) performing anion exchange chromatography and hydrophobic chromatography.

The present invention provides an industrial preparation method for a recombinant particle protein product, comprising the following steps:
(1) transfecting a host cell with a plasmid vector comprising a sequence encoding the particle protein for expression in the cell; (2) harvesting and disrupting the bacterial cells, and collecting a supernatant; (3) a. adjusting the pH of the supernatant to 7.0-8.0 and incubating the supernatant at 4-25° C. for more than 15 min, or adjusting the pH of the supernatant to 9.0-10.0 and incubating the supernatant at 4-100° C. for more than 15 min; then, after returning to room temperature, performing centrifugation, discarding a pellet, collecting a supernatant, and adding a dilution buffer to adjust the pH value to 7.0-8.0; and b. heating and incubating the solution at 50-65° C. for 5-30 min, immediately performing centrifugation, discarding a supernatant, collecting a pellet, and resuspending the pellet in a resuspension buffer at pH 9.0-11.0; and (4) performing purification by chromatographies; wherein the recombinant particle protein product is set forth in SEQ ID NO: 1.

In some embodiments, in the preparation method described above, after resuspending the pellet in step (3), urea and sodium chloride are added, followed by step (4).

In some embodiments, in any one of the preparation methods described above, in step (3)a, the pH is 8.0-10.0, and the supernatant is incubated or heated and incubated for more than 15 min at 60-90° C., 60-95° C., 60-100° C., 80-90° C., or 80-100° C. Preferably, the pH is 9.0-10.0, more preferably, the pH is 9.0; preferably, the supernatant is incubated at a temperature of 60-90° C., 80-90° C., or 80-100° C., more preferably 80-90° C.; preferably, the supernatant is incubated for a period of 15-80 min, more preferably 1 h.

In some embodiments, in any one of the preparation methods described above, in step (3)a, the pH of the supernatant is adjusted to 8.0-10.0 or 9.0-10.0, and the supernatant is heated and incubated at 60-100° C. for more than 15 min, or is heated and incubated at 80-100° C. for more than 15 min, or is heated and incubated at 80-95° C. for 15-80 min, or is heated and incubated at 80-90° C. for 15-45 min, or is heated and incubated at 60-90° C. for more than 15-60 min, or is heated and incubated at 60-95° C. for more than 15-60 min.

In some embodiments, in any one of the preparation methods described above, in step (3)a, the pH of the supernatant is adjusted to 9.0, and the supernatant is incubated at 4-95° C. for more than 15 min, or is heated and incubated at 80-95° C. for 15-80 min, or is heated and incubated at 80-90° C. for 15-45 min, or is heated and incubated at 60-90° C. for more than 15-60 min. In some embodiments, in any one of the preparation methods described above, in step (3)b, the solution is heated and incubated at a temperature of 40-90° C. for a period of 5-30 min or 5-15 min. Preferably, the solution is incubated at a temperature of 50-60° C., more preferably 60° C.; preferably, the solution is incubated for a period of 5-10 min, more preferably 10 min.

In some embodiments, in any one of the preparation methods described above, in step (3)b, the solution is heated and incubated for a period of 5-20 min, preferably 15-20 min.

In some embodiments, in any one of the preparation methods described above, in step (4), the chromatographic purification comprises both an anion exchange chromatography step and a hydrophobic chromatography step.

The present invention provides a preparation method for a recombinant particle protein product suitable for industrial production, wherein the amino acid sequence of the protein is set forth in SEQ ID NO: 1, and the preparation method comprises the following steps: (1) transfecting a host cell with a plasmid vector comprising a sequence encoding the recombinant particle protein for expression in the cell; (2) harvesting and disrupting the bacterial cells, and collecting a supernatant; (3) a. adjusting the pH of the supernatant to 9.0-10.0, incubating the supernatant at 4-100° C. for more than 15 min, returning to room temperature, then performing centrifugation, discarding a pellet, collecting a supernatant, and adding a dilution buffer to adjust the pH value to 7.0-8.0; and b. heating and incubating the solution at 50-70° C. for 5-30 min, immediately performing centrifugation, discarding a supernatant, collecting a pellet, and resuspending the pellet in a resuspension buffer at pH 7.0-11.0; (4) adding urea and sodium chloride; and (5) performing anion exchange chromatography and hydrophobic chromatography.

The present invention provides a preparation method for a recombinant particle protein product suitable for industrial production, wherein the amino acid sequence of the protein is set forth in SEQ ID NO: 1, and the preparation method comprises the following steps: (1) transfecting a host cell with a plasmid vector comprising a sequence encoding the recombinant particle protein for expression in the cell; (2) harvesting and disrupting the bacterial cells, and collecting a supernatant; (3) a. adjusting the pH of the supernatant to 9.0-10.0, heating and incubating the supernatant at 60-100° C. for more than 15 min, returning to room temperature, then performing centrifugation, discarding a pellet, collecting a supernatant, and adding a dilution buffer to adjust the pH value to 7.0-8.0; and b. heating and incubating the solution at 50-70° C. for 5-30 min, immediately performing centrifugation, discarding a supernatant, collecting a pellet, and resuspending the pellet in a resuspension buffer at pH 7.0-11.0; (4) adding urea and sodium chloride; and (5) performing anion exchange chromatography and hydrophobic chromatography.

The present invention provides a preparation method for a recombinant particle protein product suitable for industrial production, wherein the amino acid sequence of the protein is set forth in SEQ ID NO: 1, and the preparation method comprises the following steps: (1) transfecting a host cell with a plasmid vector comprising a sequence encoding the recombinant particle protein for expression in the cell; (2) harvesting and disrupting the bacterial cells, and collecting a supernatant; (3) a. adjusting the pH of the supernatant to 9.0, heating and incubating the supernatant at 80-95° C. for 15-80 min, returning to room temperature, then performing centrifugation, discarding a pellet, collecting a supernatant, and adding a dilution buffer to adjust the pH value to 7.0-8.0; and b. heating and incubating the solution at 50-70° C. for 5-30 min, immediately performing centrifugation, discarding a supernatant, collecting a pellet, and resuspending the pellet in a resuspension buffer at pH 7.0-11.0; (4) adding urea and sodium chloride; and (5) performing anion exchange chromatography and hydrophobic chromatography.

The present invention provides a preparation method for a recombinant particle protein product suitable for industrial production, wherein the amino acid sequence of the protein is set forth in SEQ ID NO: 1, and the preparation method comprises the following steps: (1) transfecting a host cell with a plasmid vector comprising a sequence encoding the recombinant particle protein for expression in the cell; (2) harvesting the bacterial cells, and disrupting the same through high-pressure homogenization; (3) a. adjusting the pH of a high-pressure homogenization supernatant to 7.0-9.0, heating and incubating the supernatant at 80-100° C. for more than 15 min, returning to room temperature, then performing centrifugation, discarding a pellet, collecting a supernatant, and adding a dilution buffer to adjust the pH value to 7.0-8.0; and b. heating and incubating the solution at 50-70° C. for 5-30 min, immediately performing centrifugation, discarding a supernatant, collecting a pellet, and resuspending the pellet in a resuspension buffer at pH 7.0-11.0; (4) adding urea and sodium chloride, wherein the urea is at a concentration of 6-8 M; and (5) performing anion exchange chromatography and hydrophobic chromatography.

The present invention provides a preparation method for a recombinant particle protein product suitable for industrial production, wherein the amino acid sequence of the protein is set forth in SEQ ID NO: 1, and the preparation method comprises the following steps: (1) transfecting a host cell with a plasmid vector comprising a sequence encoding the recombinant particle protein for expression in the cell; (2) harvesting the bacterial cells, and disrupting the same through high-pressure homogenization; (3) a. adjusting the pH of a high-pressure homogenization supernatant to 8.0-10.0, heating and incubating the supernatant at 80-95° C. for 15-80 min, returning to room temperature, then performing centrifugation, discarding a pellet, collecting a supernatant, and adding a dilution buffer to adjust the pH value to 7.0-8.0; and b. heating and incubating the solution at 50-65° C. for 5-20 min, immediately performing centrifugation, discarding a supernatant, collecting a pellet, and resuspending the pellet in a resuspension buffer at pH 7.0-11.0; (4) adding urea and sodium chloride; and (5) performing anion exchange chromatography and hydrophobic chromatography.

The present invention provides a preparation method for a recombinant particle protein product suitable for industrial production, wherein the amino acid sequence of the protein is set forth in SEQ ID NO: 1, and the preparation method comprises the following steps: (1) transfecting a host cell with a plasmid vector comprising a sequence encoding the recombinant particle protein for expression in the cell; (2) harvesting the bacterial cells, and disrupting the same through high-pressure homogenization; (3) a. adjusting the pH of a high-pressure homogenization supernatant to 7.0-8.0, heating and incubating the supernatant at 4-25° C. for more than 15 min, returning to room temperature, then performing centrifugation, discarding a pellet, collecting a supernatant, and adding a dilution buffer to adjust the pH value to 7.0-8.0; and b. heating and incubating the solution at 50-70° C. for 5-30 min, immediately performing centrifugation, discarding a supernatant, collecting a pellet, and resuspending the pellet in a buffer at pH 7.0-11.0; (4) adding urea and sodium chloride; and (5) performing anion exchange chromatography and hydrophobic chromatography.

The present invention provides a preparation method for a recombinant particle protein product suitable for industrial production, wherein the amino acid sequence of the protein is set forth in SEQ ID NO: 1, and the preparation method comprises the following steps: (1) transfecting a host cell with a plasmid vector comprising a sequence encoding the recombinant particle protein for expression in the cell; (2) harvesting the bacterial cells, and disrupting the same through high-pressure homogenization; (3) a. adjusting the pH of a high-pressure homogenization supernatant to 9.0; incubating the supernatant at 4-95° C. for more than 15 min; preferably, heating and incubating the supernatant at 60-90° C. for 15-60 min, more preferably, heating and incubating the supernatant at 80-90° C. for 15-45 min; then, after returning to room temperature, performing centrifugation, discarding a pellet, collecting a supernatant, and adding a dilution buffer to adjust the pH value to 7.0-8.0; and b. heating and incubating the solution at 50-70° C. for 5-30 min, immediately performing centrifugation, discarding a supernatant, collecting a pellet, and resuspending the pellet in a resuspension buffer at pH 7.0-11.0; (4) adding urea and sodium chloride; and (5) performing anion exchange chromatography and hydrophobic chromatography.

The present invention further provides a recombinant particle protein product, which is prepared by any one of the preparation methods described above.

In some embodiments, in any one of the recombinant particle protein products or the preparation methods therefor described above, the dilution buffer comprises Tris-hydrochloric acid, acetic acid-sodium acetate, citric acid, or phosphoric acid, which is at a pH of 6.5-8.0 and at a concentration of 50-100 mM, preferably 70 mM, 80 mM, 90 mM, or 100 mM. The dilution buffer may also comprise ethylenediaminetetraacetic acid (EDTA) at a concentration of 5-20 mM. The dilution buffer may also comprise a detergent, such as: polyethylene glycol octyl phenyl ether, Tween® (Tween® 20 or Tween® 80), SDS, Triton® X-100, NP-40, or the like. The dilution buffer preferably comprises Tris-hydrochloric acid, ethylenediaminetetraacetic acid, and Triton® X-100. The buffer is at a concentration of 0.1%-8%, preferably at a concentration of 2%, 3%, 4%, or 5%.

In some embodiments, in any one of the recombinant particle protein products or the preparation methods therefor described above, the resuspension buffer comprises Tris-hydrochloric acid, acetic acid-sodium acetate, citric acid, or phosphoric acid, which is at a pH of 2.5-10.0 and at a concentration of 20-100 mM, preferably 70 mM, 80 mM, 90 mM, or 100 mM. The dilution buffer may also comprise ethylenediaminetetraacetic acid (EDTA) at a concentration of 5-20 mM, and preferably comprises Tris-hydrochloric acid and ethylenediaminetetraacetic acid.

In some embodiments, in any one of the recombinant particle protein products or the preparation methods therefor described above, the host cells used for expressing the recombinant particle protein may be any conventionally used host cells to which genetic engineering methods are applied to produce recombinant proteins, including, but not limited to: human embryonic kidney cells (e.g., HEK293), Chinese hamster ovary cells (CHO and various subtypes thereof, e.g., CHO-K1, CHO-S, and CHO-GS cells with a glutamine synthetase system), African green monkey kidney fibroblasts (e.g., COS-7), E. coli (DH5a, BL21, and DH10B), and the like.

In some embodiments, in any one of the recombinant particle protein products or the preparation methods therefor described above, a culture medium used for the cells may be any culture medium known in the art that is suitable for the expression of exogenous proteins in CHO, HEK, or E. coli, including, but not limited to: CD CHO, Dynamis, CD02, CD04, CD05, ExpiCHO, DMEM, FreeStyle 293, Luria Broth, Terrific Broth, and other culture media.

In some embodiments, in any one of the recombinant particle protein products or the preparation methods therefor described above, the urea is used at a concentration of 0.5-10 M; preferably, the urea may be used at a concentration of 4 M, 4.5 M, 5 M, 5.5 M, 6 M, 6.5 M, 7 M, 7.5 M, 8 M, or 8.5 M, more preferably 6-8 M; the sodium chloride is used with a final concentration of 10-200 mM; preferably, the sodium chloride may be used with a final concentration of 50-200 mM.

In some embodiments, in any one of the recombinant particle protein products or the preparation methods therefor described above, a medium used in the anion exchange chromatography may be any feasible medium, including, but not limited to: DEAE Sepharose™ FF, Q Sepharose™ FF, Capto™ DEAE, Capto™ Q Impres, POROS™ HQ, POROS™ 50D, POROS™ PI, Fractogel® DEAE, or Fractogel® TMAE, preferably Fractogel® DEAE.

In some embodiments, in any one of the recombinant particle protein products or the preparation methods therefor described above, a medium used in the hydrophobic chromatography may be any feasible medium, including, but not limited to: Butyl-S Sepharose™ 6FF, Butyl Sepharose™ 4 FF, Octyl Bestarose 4FF, Phenyl Sepharose™ 6FF, Capto™ Butyl, Capto™ Phenyl, Capto™ Phenyl Impres, or Capto™ Octyl, preferably Octyl Bestarose 4FF.

In some embodiments, in any one of the recombinant particle protein products or the preparation methods therefor described above, a stabilizer is added to a collected elution fraction obtained from the anion exchange chromatography and to a buffer in the hydrophobic chromatography, wherein the stabilizer is selected from an amino acid, a polyol, or a saccharide, wherein the amino acid is preferably arginine, glycine, or histidine, the saccharide is preferably sucrose or trehalose, the polyol is preferably glycerol or sorbitol, and the stabilizer is at a concentration of more than 20% (w/v).

All reagents used in the present invention are commercially available.

Beneficial Effects of Present Invention

By using the method of the present invention, the purity of the sample obtained before chromatography can reach more than 85% before chromatography, thereby reducing chromatography steps and pressure, improving production efficiency, and saving cost of large-scale production. Using urea at a high concentration and sodium chloride at a specific concentration can significantly reduce impurities and improve the impurity removal effect. According to the method of the present invention, a product with uniform particle size, good batch-to-batch consistency in particle size, low impurity residues, and no solvent residues can be obtained.

In conclusion, the preparation method for the recombinant particle protein product provided by the present invention is simple to operate and can reduce the amount of organic solvents used in subsequent chromatographic purification, thus reducing the cost of large-scale industrial production, and being suitable for industrial production; thanks to the product prepared by using the recombinant particle protein provided by the present invention, the side effects caused by the residues of impurities, host proteins, organic solvents, exogenous DNAs, antibiotics, bacterial endotoxins, and other substances in the particles are effectively reduced, thereby improving the safety.

BRIEF DESCRIPTION OF THE DRAWINGS

FIG. 14 shows an SDS-PAGE analysis of F-DEAE chromatography after KCl and $Na_2SO_4$ soaking treatments in Example 4.

DETAILED DESCRIPTION

The principles and features of the present invention are described with reference to the following examples, and the examples provided are only intended to explain the present invention and are not intended to limit the scope of the present invention. Before the detailed description of the present invention is further provided, it should be understood that the protection scope of the present invention is not limited to the specific embodiments described below; it should also be understood that the terminology used in the examples herein is intended to describe specific embodiments and is not intended to limit the protection scope of the present invention. Test procedures without specified conditions in the following examples are generally conducted according to conventional conditions or according to conditions recommended by manufacturers. When numerical ranges are given in the examples, it should be understood that, unless otherwise specified in the present invention, both endpoints of each of the numerical ranges and any numerical value between the two endpoints can be selected. Unless otherwise defined, all technical and scientific terms used herein have the same meaning as commonly understood by those skilled in the art. In addition to the specific methods, equipment, and materials used in the examples, any methods, equipment, and materials similar or equivalent to those described in the examples herein can also be used to implement the present invention, based on the understanding of the prior art by those skilled in the art and the disclosure of the present invention.

Example 1. Determination of First-Step Heating Process Conditions for Recombinant Particle Protein in *E. coli* Lysate Supernatant A host cell was transfected with a plasmid comprising a sequence encoding the target recombinant particle protein using a conventional method for expression in the cell. The bacterial cells were harvested and then disrupted through high-pressure homogenization to release the target protein. The amino acid sequence of the target recombinant particle protein is set forth in SEQ ID NO: 1.

Figure 1:
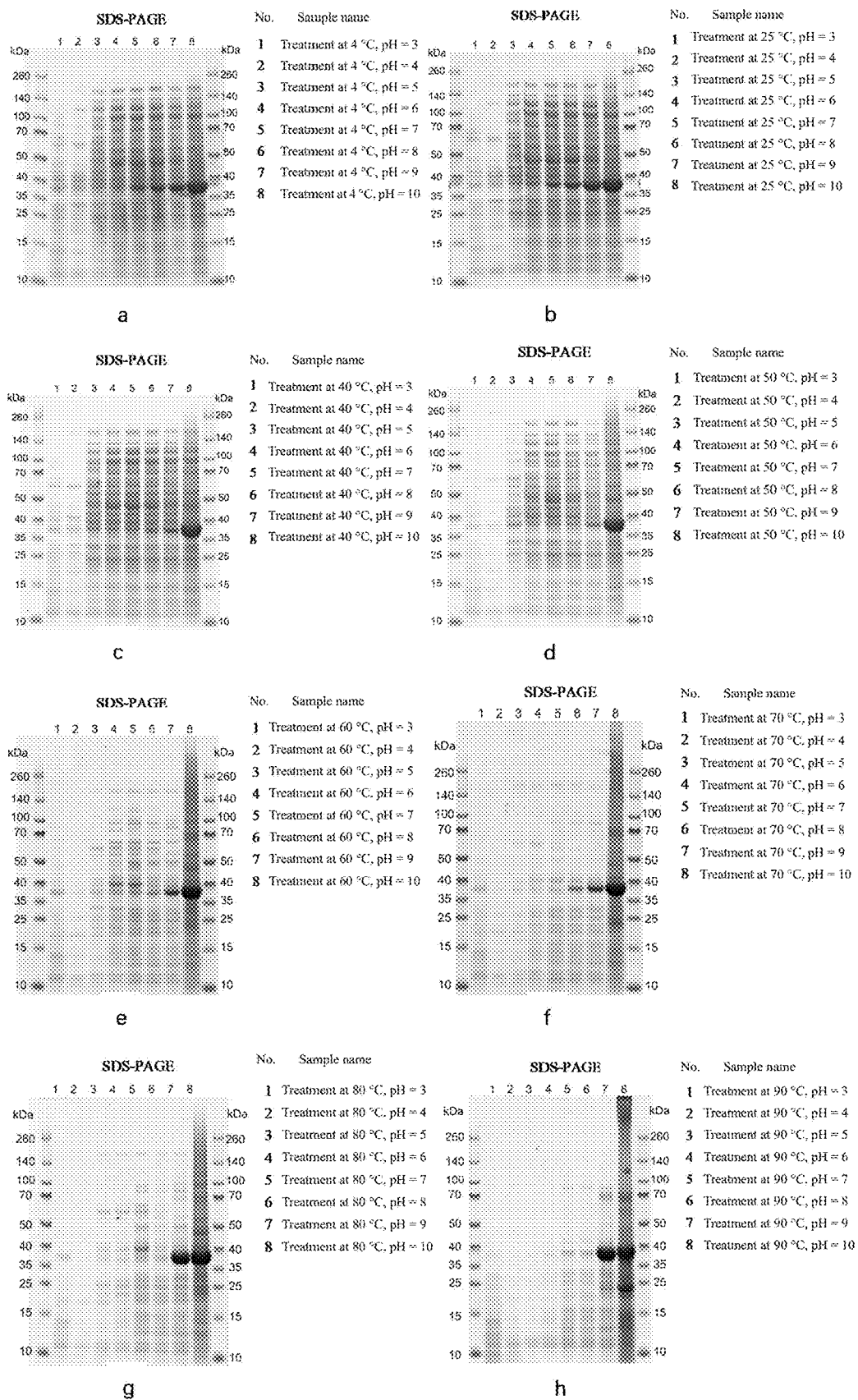
FIG. 1 shows SDS-PAGE images of supernatants obtained by centrifugation of bacterial cell lysate supernatants treated under different temperature and pH conditions in Example 1.

1. Effects of Different pH and Temperature Conditions on the Solubility of Recombinant Particle Protein in the Bacterial Cell Lysate Supernatant For the pH, the following 8 investigation points were set: pH 3.0, pH 4.0, pH 5.0, pH 6.0, pH 7.0, pH 8.0, pH 9.0, and pH 10.0. For the temperature, the following 8 investigation points were set: 4° C., 25° C., 40° C., 50° C., 60° C., 70° C., 80° C., and 90° C. An *E. coli* bacterial cell lysate supernatant was used as a sample, which was subjected to pH adjustment under conditions shown in Table 1 and Table 2. The resulting samples with different pH values were each incubated at 4° C., 25° C., 40° C., 50° C., 60° C., 70° C., 80° C. and 90° C. for 60 min, followed by immediate centrifugation at 15000 g for 15 min. The supernatants were then collected and subjected to SDS-PAGE detection, and the results are shown in FIG. 1.

TABLE 1 pH adjustment conditions for samples incubated at 4-70° C.

| Set pH value | Actual pH value, buffer temperature | pH-adjusting buffer |
| --- | --- | --- |
| 3 | 3.3, 24.6° C. | Glycine-HCl, pH 2.5 |
| 4 | 4.1, 24.6° C. | NaAc—HAc, pH 3.8 |
| 5 | 5.2, 24.9° C. | NaAc—HAc, pH 5.0 |
| 6 | 6.3, 24.9° C. | Na$_2$HPO$_4$—NaH$_2$PO$_4$, pH 6.0 |
| 7 | 6.9, 24.9° C. | Na$_2$HPO$_4$—NaH$_2$PO$_4$, pH 6.5 |
| 8 | 7.9, 25.4° C. | Tris-HCl, pH 8.0 |
| 9 | 8.8, 24.9° C. | Tris-HCl, pH 9.0 |
| 10 | 9.9, 25.2° C. | NaHCO$_3$—Na$_2$CO$_3$, pH 10.0 |

TABLE 2 pH adjustment conditions for samples incubated at 80° C. and 90° C.

| Set pH value | Actual pH value, buffer temperature | pH-adjusting buffer |
| --- | --- | --- |
| 3 | 3.3, 22.0° C. | Glycine-HCl, pH 2.5 |
| 4 | 4.1, 24.6° C. | NaAc—HAc, pH 3.8 |
| 5 | 5.3, 24.9° C. | NaAc—HAc, pH 5.0 |
| 6 | 6.0, 23.2° C. | Na$_2$HPO$_4$—NaH$_2$PO$_4$, pH 6.0 |
| 7 | 7.0, 23.4° C. | Na$_2$HPO$_4$—NaH$_2$PO$_4$, pH 6.5 |
| 8 | 7.9, 23.8° C. | Tris-HCl, pH 8.0 |
| 9 | 9.0, 23.6° C. | Tris-HCl, pH 9.0 |
| 10 | 9.9, 24.1° C. | NaHCO$_3$—Na$_2$CO$_3$, pH 10.0 |

Results and Analysis:

As can be seen from FIG. 1, when the pH was 3.0, 4.0, 5.0, or 6.0, no obvious bands of the target recombinant particle protein could be distinguished in the centrifugation supernatants after treatment for 1 h under all temperature conditions, and in the process of adjusting the pH to 3.0, 4.0, 5.0, and 6.0, a large amount of light yellow pellet appeared in the bacterial cell lysate supernatants and could not be redissolved, indicating that at pH 3.0-6.0, regardless of temperature changes from 4° C. to 90° C., the solubility of the recombinant particle protein was extremely low.

At pH 7.0 and 8.0, when the treatment temperature was 4° C., 25° C., 40° C., or 50° C., bands of the recombinant particle protein appeared in the supernatants, but the band gray value was lower than that of the samples at pH 9.0 or 10.0 under the same temperature. It is speculated that at pH 7.0 or 8.0, with treatment at 4° C., 25° C., 40° C., or 50° C. for 1 h, the recombinant particle protein exhibited a certain solubility in the bacterial sludge lysate, but the solubility did not reach its maximum and there were many impurity proteins present. As can be observed from FIGS. 1*e/f/g/h*, after treatment at 60° C., 70° C., 80° C., and 90° C. for 1 h, there were fewer impurity proteins under the pH 8.0 condition compared to the pH 7.0 condition.

After 1 hour of incubation at 4° C., 25° C., 40° C., 50° C., 60° C., 70° C., 80° C. and 90° C., the content of the recombinant particle protein in the supernatant was significantly higher at pH 9.0 compared to other pH groups, indicating that the solubility of the recombinant particle protein was better at pH 9.0 than at other pH values. The concentration of the recombinant particle protein in the supernatant after 1 hour of treatment at 80° C. and 90° C. was higher than that in other temperature treatment groups, and the electrophoresis results indicate that the impurity content in the samples was also lower. At pH 9.0, the content of the recombinant particle protein in the centrifugation supernatant after treatment at 40° C. and 50° C. was significantly lower than that after treatment at 4° C. and 25° C., but the content of the recombinant particle protein in the supernatant was increased again in the 60° C. and 70° C. treatment groups, with the highest solubility observed at 80° C. and 90° C. This indicates that at pH 9.0, there was an inflection point in the solubility of the recombinant particle protein between 50° C. and 60° C.; between 4° C. and the inflection point temperature, the solubility of the recombinant particle protein decreased as the temperature increased; between the inflection point temperature and 90° C., the solubility of the recombinant particle protein increased as the temperature increased.

At pH 10.0, a large amount of recombinant particle protein was present in the supernatant after treatment at different temperatures from 4° C. to 90° C. for 1 h, indicating that the solubility of the recombinant particle protein was relatively high at this pH; meanwhile, a relatively larger amount of impurity proteins were observed in the supernatant.

In summary, during the first-step heating treatment, the solubility of the recombinant particle protein in the resuspension of E. coli bacterial cells under different pH and temperature conditions exhibited the following characteristics:

a) under slightly acidic conditions (pH 3.0-6.0), the solubility of the recombinant particle protein was relatively low no matter what temperature was adopted for treatment;
b) under the pH 7.0 condition, although the recombinant particle protein exhibited a certain solubility under incubation at 4-90° C., there were many impurities and the impurity removal effect was poor;
c) under the pH 8.0 condition, when the heating treatment was performed at 60-90° C., the impurity removal effect was relatively significant, and the purity of the recombinant particle protein was relatively high;
d) at pH 9.0, the recombinant particle protein exhibited higher solubility compared to lower pH values at 4-90° C., with the highest solubility and the best impurity removal effect observed at 80-90° C.; there was an inflection point in the solubility of the recombinant particle protein at pH 9.0 between 50° C. and 60° C.; and
e) at pH 10.0, the recombinant particle protein exhibited extremely high solubility between 4° C. and 90° C.; meanwhile, the solubility of impurities was relatively slightly higher, and the impurity removal effect was slightly poorer compared to pH 9.0, but the overall purification effect was not affected.

2. Effects of different heating durations on the solubility of recombinant particle protein in the bacterial cell lysate supernatant Further study on the heating duration was conducted to determine the heating time limit for achieving relatively high solubility of the recombinant particle protein:

An E. coli bacterial cell lysate supernatant was used as a sample, which was adjusted to pH 9.0 and then aliquoted. The aliquots were heated and incubated at 80° C. and 90° C., respectively, with three heating duration investigation points set at 15 min, 30 min, and 45 min. After incubation, the aliquots were immediately centrifuged at 15000 g for 15 min. The supernatants were then collected and subjected to SDS-PAGE detection, and the detection results are shown in FIG. 2.

Figure 2:
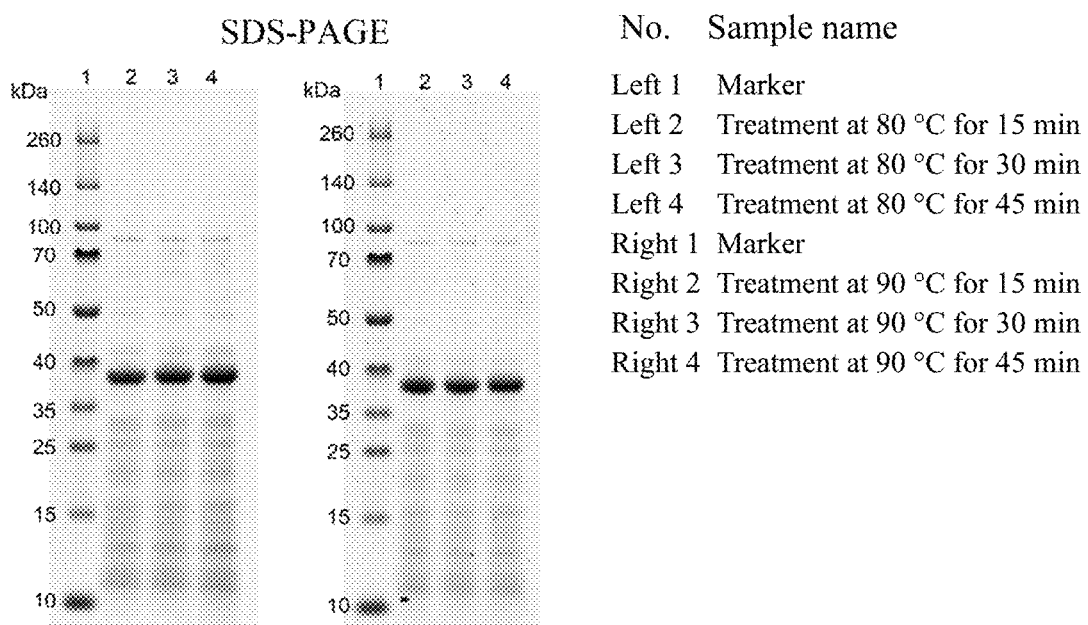
FIG. 2 shows SDS-PAGE images of supernatants obtained by centrifugation of bacterial cell lysate supernatants treated with different heating durations in Example 1.

Results and Analysis:

As can be seen from FIG. 2, the centrifugation supernatants after incubation at pH 9.0 and 80-90° C. for 15 min, 30 min, and 45 min showed significant bands of the recombinant particle protein. Compared to the condition of heating and incubation for 1 h, it was found that after heating for 15-45 min, the band gray value of the supernatant was slightly lower than that after heating for 1 h, and the impurity removal effect was similar to that after heating at 60-90° C. for 1 h. It can be seen that at 80-90° C. and pH 9.0, after heating for 15 min, 30 min, and 45 min, the recombinant particle protein could also exhibit relatively high solubility, while still maintaining relatively good impurity removal effect.

After the first-step heating treatment (e.g., pH=9.0, heating and incubation treatment at 80-90° C. for 1 h), the purity of the recombinant protein could reach more than 60%.

In summary, the purity of the recombinant particle protein could be improved by treating the recombinant particle protein product with the first-step heating process. Based on the solubility and purity state of the recombinant particle protein under different conditions, the first-step heating process conditions were determined to be 60-90° C., heating and incubation for more than 15 min, and pH 8.0-10.0, with the preferred conditions being 80-90° C., heating and incubation for 1 h, and pH 9.0.

Example 2. Determination of Second-Step Heating Process Conditions for Recombinant Particle Protein in E. coli Lysate Supernatant The E. coli bacterial cell lysate underwent the first-step heating treatment to separate impurities and the recombinant particle protein. The sample is then subjected to a second-step heating treatment to further separate impurities and the recombinant particle protein. Based on the first-step heating, the effects of treatment temperature and duration on the solubility of the recombinant particle protein and impurities were explored under the pH 7.4 condition.

First-step heating: A bacterial cell lysate supernatant was taken, adjusted to pH 9.0, then heated at 80° C. for 1 h, and centrifuged at 12000 g and 4° C. for 30 min to collect a supernatant. An equal volume of a pH 7.4 buffer containing 100 mM Tris-HCl, 5 mM EDTA, and 4% Triton® X-100 was added to the resulting supernatant, and 10% of the total volume of 1 M Tris-HCl pH 7.4 buffer was added.

Figure 3:
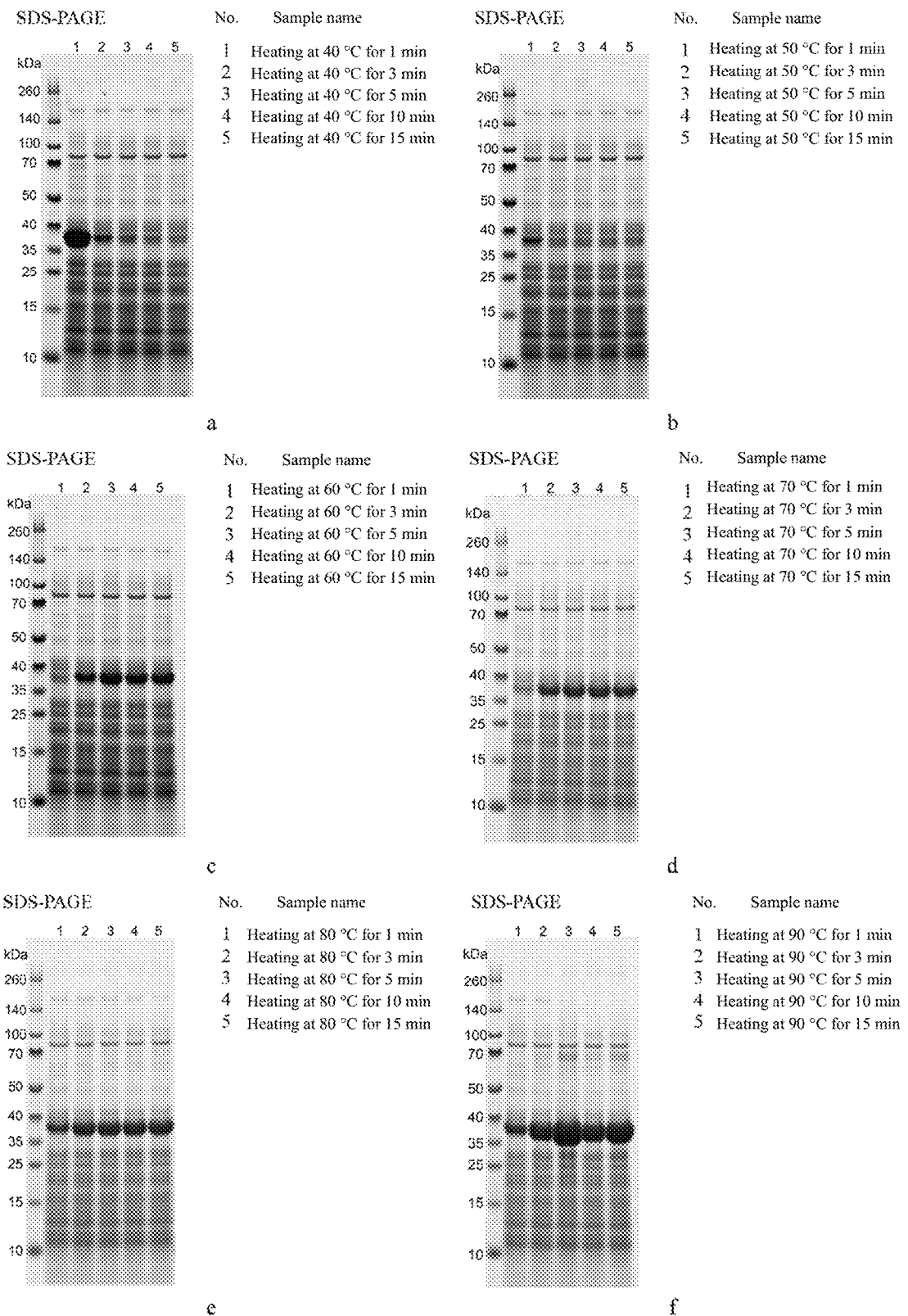
FIG. 3 shows SDS-PAGE images of supernatants obtained by centrifugation after treatment with different temperatures and heating durations in the second step for heating and impurity removal in Example 2.

Second-step heating: For the heating temperature, the following 6 investigation points were set up: 40° C., 50° C., 60° C., 70° C., 80° C., and 90° C. For the heating duration, the following 5 investigation points were set up: 1 min, 3 min, 5 min, 10 min, and 15 min. Pre-treated samples were heated at 40° C., 50° C., 60° C., 70° C., 80° C. and 90° C. for 1 min, 3 min, 5 min, 10 min and 15 min, followed by immediate centrifugation at 15000 g for 60 s to collect supernatants. The supernatants were then subjected to SDS-PAGE detection, and the detection results are shown in FIG. 3.

Results and Analysis:

As can be seen from FIG. 3a/b, under the heating conditions of 40° C. and 50° C., the recombinant particle protein was completely pelleted after 3 minutes of heating, leaving no recombinant particle protein in the supernatants; during the first 3 minutes of heating, the supernatants still showed bands of the recombinant particle protein, which presumably resulted from the fact that the sample temperature had not risen to the set temperature due to the relatively short heating duration. As can be seen from FIG. 3c/d/e/f, under the heating conditions of 60° C., 70° C., 80° C. and 90° C., the content of the recombinant particle protein in the supernatants increased with the heating duration during the first 3 min; additionally, the solubility of the recombinant particle protein increased as the heating temperature rose, and did not change after 5 minutes of heating.

After the second-step heating treatment (e.g., pH=7.4, heating and incubation treatment at 60° C. for 10 min), the purity of the recombinant protein could reach more than 85%.

In summary, the samples that underwent the first-step heating treatment, when subjected to the second-step heating, exhibited the following characteristics:

a) the recombinant particle protein exhibited the lowest solubility at 50° C., and the electrophoresis showed that the impurity proteins still existed in the supernatant; and b) when the recombinant particle protein was heated at 60-90° C., the higher the temperature, the higher the solubility of the recombinant particle protein.

In summary, the second-step heating process conditions for the recombinant particle protein product were 40-90° C., heating and incubation treatment for 5-15 min, and pH 7.0-8.0, with the preferred conditions being 50-60° C., heating and incubation treatment for 5-10 min, and pH 7.4.

Figure 4:
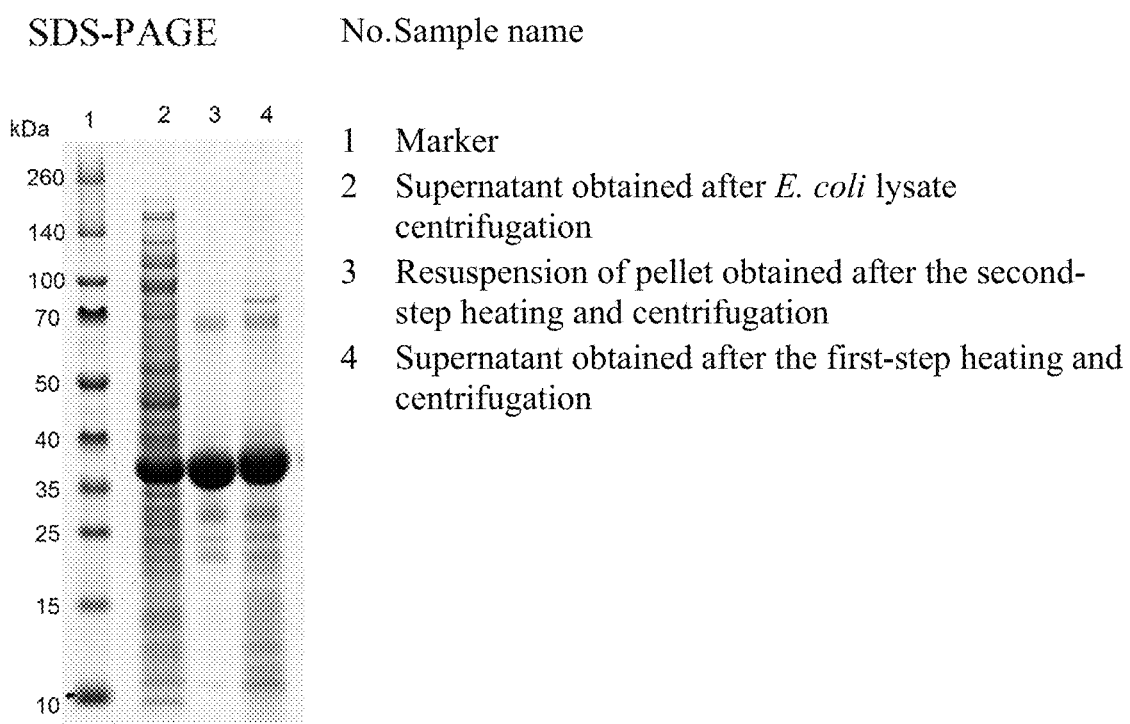
FIG. 4 shows an SDS-PAGE image for the purities after two-step heating in Example 3.

Example 3. Two-Step Heating Preparation Process for Recombinant Particle Protein Product The recombinant particle protein was expressed in *E. coli*. The bacterial cells were harvested and then disrupted through high-pressure homogenization to release the target protein. The feed liquid was clarified, with the main purpose of removing bacterial cell debris and impurity proteins. The clarification of the feed liquid was mainly achieved by heating treatment. Using the methods from Example 1 and Example 2 to perform heating treatment, the *E. coli* lysate supernatant was subjected to first-step heating and second-step heating (i.e., "two-step heating"). The impurity removal effect and the purity of the recombinant particle protein in the two-step heating process were measured. 60 g of wet *E. coli* bacterial cells collected by centrifugation were taken, resuspended in 240 mL of a buffer (20 mM Tris-HCl, 2 mM PMSF, pH=9.0), and disrupted using a high-pressure homogenizer at 1000 bar. After centrifugation, 280 mL of supernatant was collected. 40 mL of the resulting supernatant was then taken and subjected to the two-step heating operation. The lysate supernatant, the supernatant obtained after the first-step heating and centrifugation, and the resuspension of pellet obtained after the second-step heating and centrifugation were subjected to SDS-PAGE analysis (as shown in FIG. 4). FIG. 4 shows the SDS-PAGE detection results for the *E. coli* lysate supernatant, the supernatant obtained after the first-step heating, and the resuspension of pellet obtained after the second-step heating.

Results and Analysis:

Through experiments on the recombinant particle protein under different temperature and pH conditions, it was found that the particle protein could maintain high stability and high solubility under high-temperature conditions, and could also form a resoluble pellet under specific pH conditions.

Specifically, as shown in Table 3, in the first-step heating treatment, the pH was adjusted to 9.0, and the sample was heated in a water bath at 80° C. for 1 h, returned to room temperature, and then centrifuged to collect a supernatant (about 35 mL). In the second-step heating treatment, 35 mL of a pH 7.4 buffer containing 100 mM Tris-HCl, 5 mM EDTA, and 4% Triton® X-100 was added, and then 7 mL of 1 M Tris-HCl pH 7.4 was added. The mixture was well mixed, heated in a water bath at 60° C. for 10 min, and then immediately centrifuged to collect a pellet. The pellet was then redissolved in a pH 9.0 buffer containing 20 mM Tris-HCl and 5 mM EDTA.

TABLE 3

Two-step heating extraction process for recombinant particle protein product

| Procedures | Reaction conditions | Operational values |
|---|---|---|
| First pelleting and centrifugation | Heating temperature | 80° C. |
| | Heating duration | 60 min |
| | Centrifugation rotation speed | 12000 g |
| | Centrifugation temperature | 4° C. |
| | Centrifugation time | 30 min |
| Supernatant dilution | Dilution buffer | 100 mM Tris-HCl, 5 mM EDTA, 4% Triton ® X-100, pH 7.4 |
| | Volume of dilution buffer | 1:1 (v/v) |
| | pH buffer | 1M Tris-HCl, pH 7.4 |
| | Volume of pH buffer | 10% of the total volume |
| Second pelleting and centrifugation | Heating temperature | 60° C. |
| | Heating duration | 10 min |
| | Centrifugation rotation speed | 6000 g |
| | Centrifugation temperature | 30° C. |
| | Centrifugation time | 10 min |
| Pellet resuspension | Resuspension buffer | 20 mM Tris-HCl, 5 mM EDTA, pH 9.0 |
| | Volume of resuspension buffer | Resuspending to pre-centrifugation volume |
| | pH | 9.0 ± 0.1 |
| | Filtration | 0.22 μm |

In summary, before the chromatography operation, the purity of the recombinant particle protein could be improved to more than 85% through the two-step heating process, thereby lowering the pressure of subsequent chromatographic purification and reducing the required chromatography procedures and production cost.

Example 4. Combined Preparation Process for Recombinant Particle Protein Product with Urea and Sodium Chloride After the two-step heating process, adding urea and sodium chloride at different concentrations before chromatographic purification could significantly reduce the presence of unidentified substances near the target recombinant particle protein bands. The optimum urea treatment time and sodium chloride concentration were determined through experiments.

1. Urea treatment:
   (1) For urea treatment, six treatment conditions, namely a 6 M urea short-time soaking group (1 h), a 6 M urea overnight soaking group (17 h), a 4 M urea short-time soaking group (1 h), a 4 M urea overnight soaking group (17 h), a 1 M urea short-time soaking group (1 h), and a 1 M urea overnight soaking group (17 h), were set up:

A bacterial cell lysate supernatant was taken, adjusted to pH 9.0, then heated at 80° C. for 1 h, and centrifuged at 12000 g and 4° C. for 30 min to collect a supernatant. An equal volume of a pH 7.4 buffer containing 100 mM Tris-HCl, 5 mM EDTA, and 4% Triton® X-100 was added to the resulting supernatant, and 10% of the total volume of 1 M Tris-HCl pH 7.4 buffer was added. The mixture was heated at 60° C. for 10 min and immediately centrifuged at 6000 g for 10 min, and the supernatant was removed. The pellet was redissolved in a pH 9.0 buffer containing 20 mM Tris-HCl and 5 mM EDTA.

Six groups, namely a 6 M urea short-time soaking group (1 h), a 6 M urea overnight soaking group (17 h), a 4 M urea short-time soaking group (1 h), a 4 M urea overnight soaking group (17 h), a 1 M urea short-time soaking group (1 h), and a 1 M urea overnight soaking group (17 h), were set up. The recombinant particle protein samples of the present application after treatment with urea were subjected to size exclusion chromatography analysis, and the small molecule impurity peaks following the main peaks of the protein samples were subjected to SDS-PAGE detection to determine their composition, so that the impurity removal effect of each group was further determined.

Figure 5:
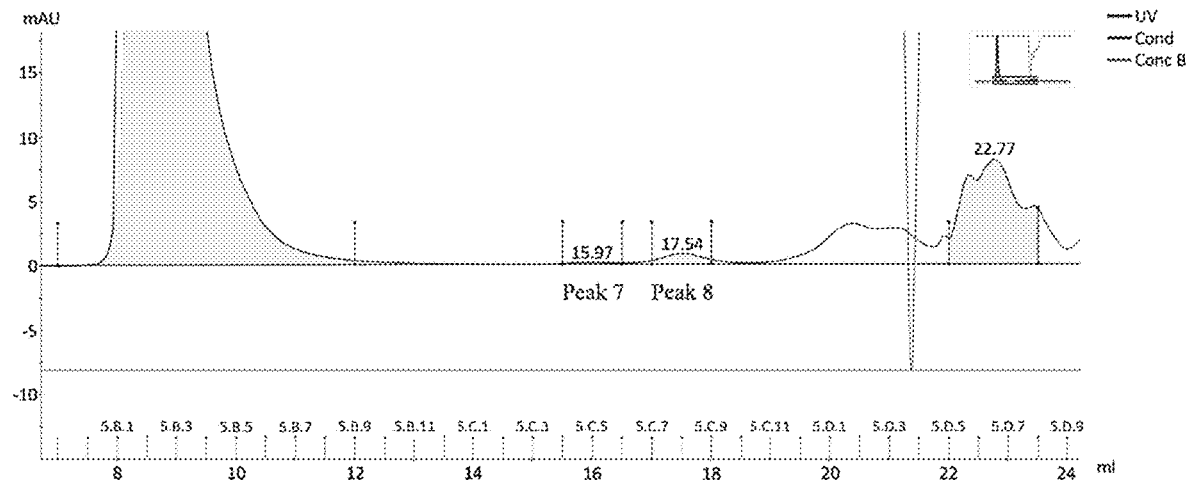
FIG. 5 shows size exclusion chromatograms for soaking treatment with 6 M urea in Example 4.
Figure 5:
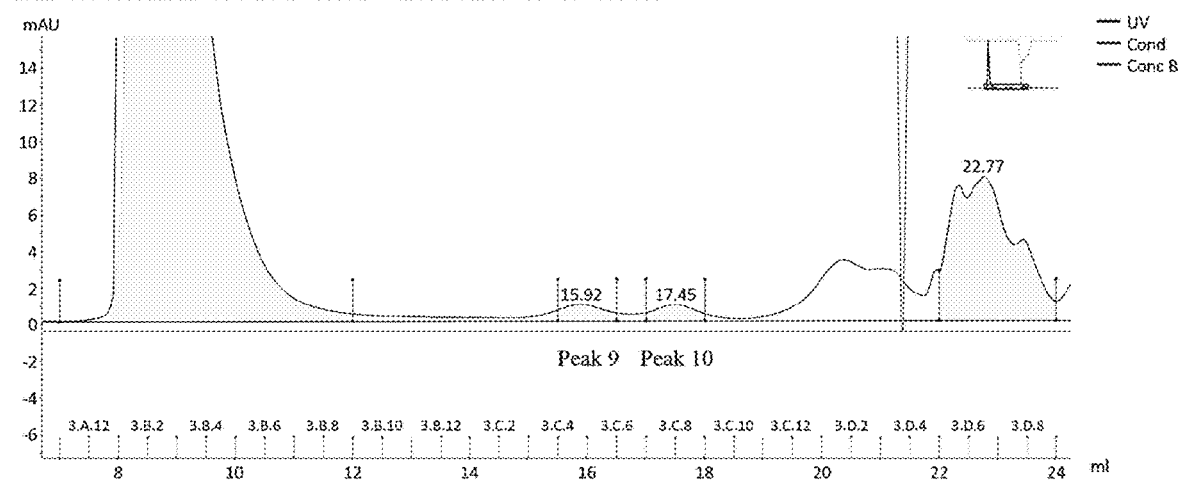
Figure 6:
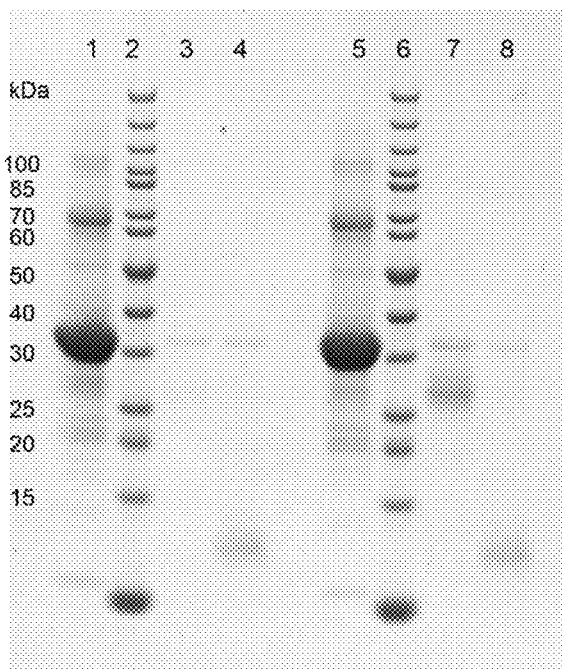
FIG. 6 shows SDS-PAGE detection results of size exclusion elution peaks after treatment with 6 M urea in Example 4.
Figure 7:
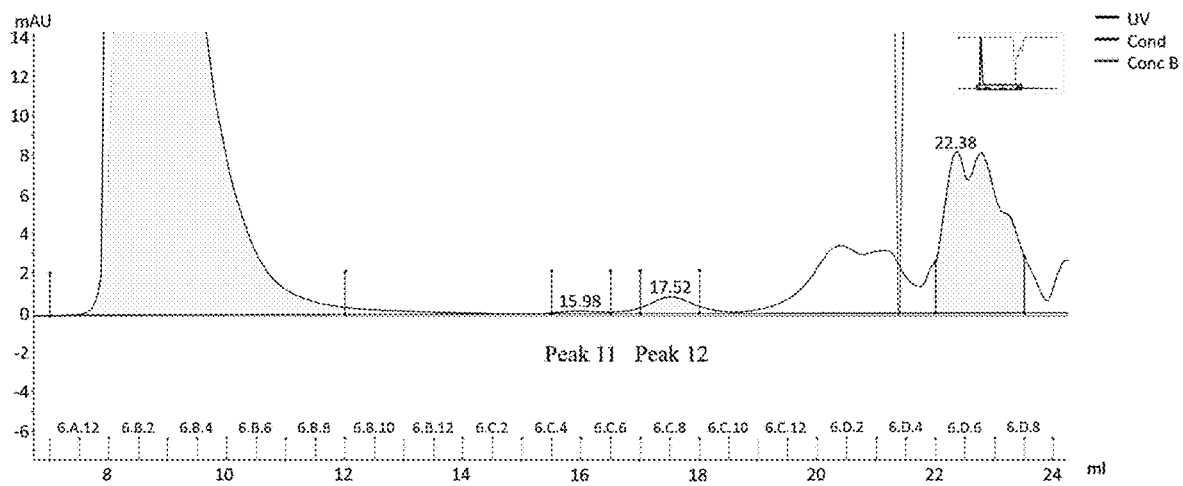
FIG. 7 shows size exclusion chromatograms for soaking treatment with 4 M urea in Example 4.
Figure 7:
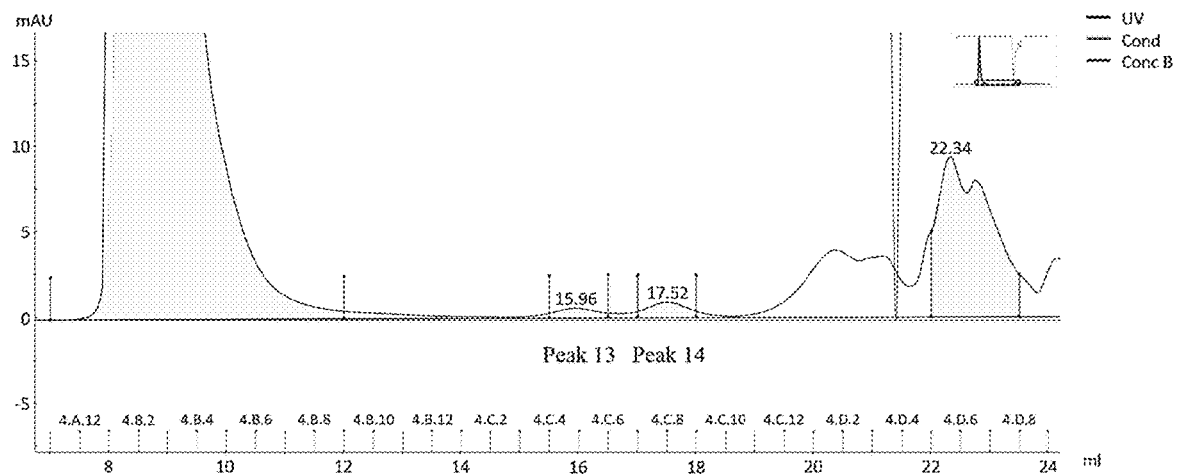
Figure 8:
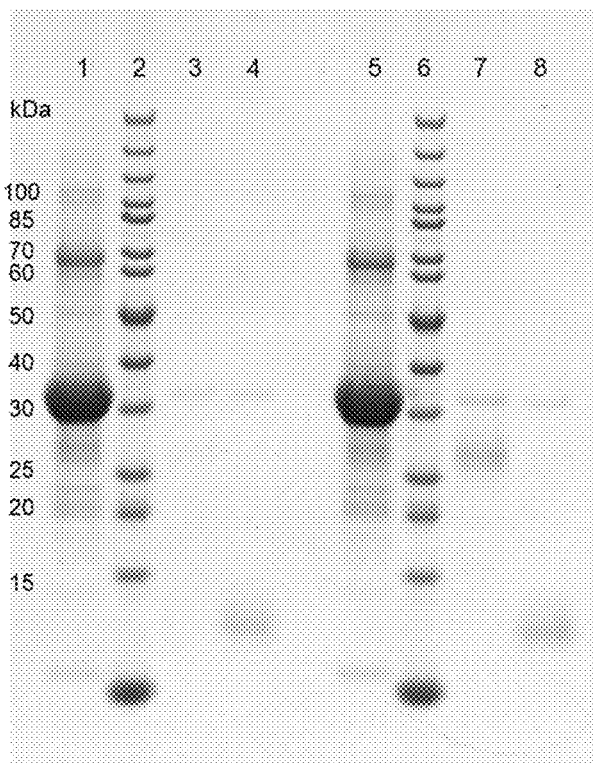
FIG. 8 shows SDS-PAGE detection results of size exclusion elution peaks after treatment with 4 M urea in Example 4.
Figure 9:
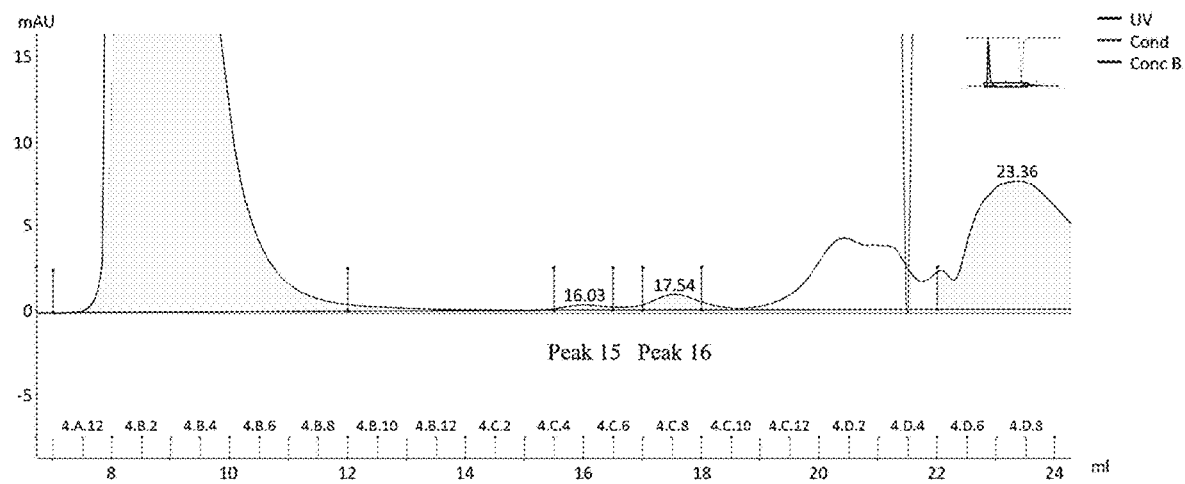
FIG. 9 shows size exclusion chromatograms for soaking treatment with 1 M urea in Example 4.
Figure 9:
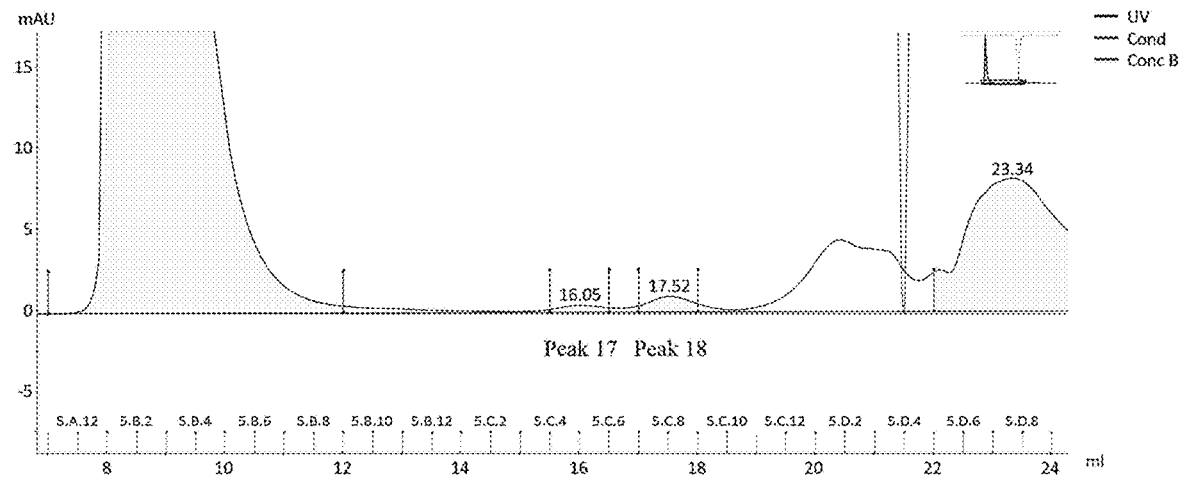
Figure 10:
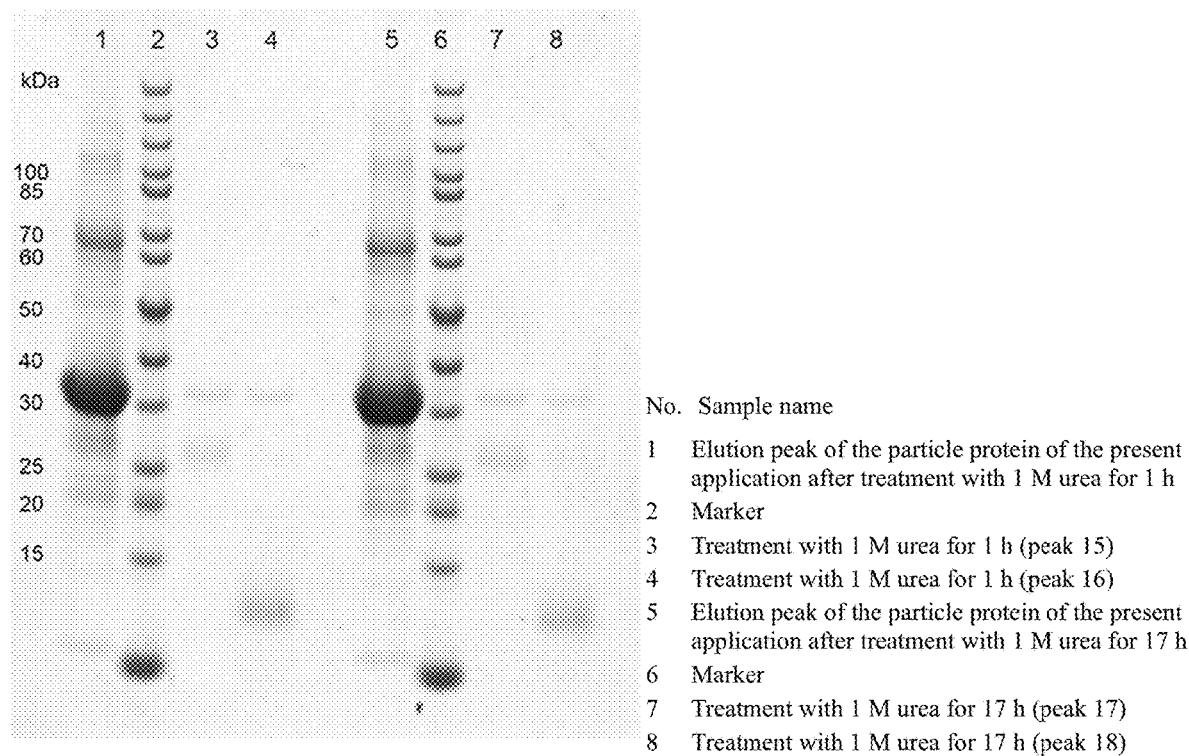
FIG. 10 shows SDS-PAGE detection results of size exclusion elution peaks after treatment with 1 M urea in Example 4.

Results and Analysis:

The size exclusion chromatograms for soaking treatment with 6 M urea are shown in FIG. 5; the SDS-PAGE detection results of size exclusion elution peaks after treatment with 6 M urea are shown in FIG. 6; the size exclusion chromatograms for soaking treatment with 4 M urea are shown in FIG. 7; the SDS-PAGE detection results of size exclusion elution peaks after treatment with 4 M urea are shown in FIG. 8; the size exclusion chromatograms for soaking treatment with 1 M urea are shown in FIG. 9; the SDS-PAGE detection results of size exclusion elution peaks after treatment with 1 M urea are shown in FIG. 10.

As can be seen from the chromatograms, after treatment with urea at three different concentrations for 1 h and 17 h, other substances with a molecular weight smaller than that of the main peak of the recombinant particle protein of the present application (peaks 7-18) could be separated in the size exclusion. Additionally, it was found that in all three 17-hour soaking treatment groups, the impurity peak height was 1.13 mAU for the 6 M urea treatment, 0.54 mAU for the 4 M urea treatment, and 0.30 mAU for the 1 M urea treatment. This indicates that, for the same treatment time, the higher the urea concentration, the greater the separation and removal effect on the impurities. In summary, it can be concluded that, for the same treatment time, the separation and removal effect on the impurities increased as the urea concentration increased.

(2) Further, three treatment conditions, namely a urea-free control group, an 8 M urea short-time soaking group (1 h), and an 8 M urea overnight soaking group (16-18 h), were set up:

A bacterial cell lysate supernatant was taken, adjusted to pH 9.0, then heated at 80° C. for 1 h, and centrifuged at 12000 g and 4° C. for 30 min to collect a supernatant. An equal volume of a pH 7.4 buffer containing 100 mM Tris-HCl, 5 mM EDTA, and 4% Triton® X-100 was added to the resulting supernatant, and 10% of the total volume of 1 M Tris-HCl pH 7.4 buffer was added. The mixture was heated at 60° C. for 10 min and immediately centrifuged at 6000 g for 10 min, and the supernatant was removed. The pellet was redissolved in a pH 9.0 buffer containing 20 mM Tris-HCl and 5 mM EDTA.

Three treatment conditions, namely a urea-free control group, an 8 M urea short-time soaking group (1 h), and an 8 M urea overnight soaking group (16-18 h), were set up. The treated samples were subjected to substance separation using size exclusion chromatography (as shown in FIG. 11), and the small molecule peaks following the main peak of the recombinant particle protein were subjected to SDS-PAGE detection to determine their molecular weights (as shown in FIG. 12).

Figure 11:
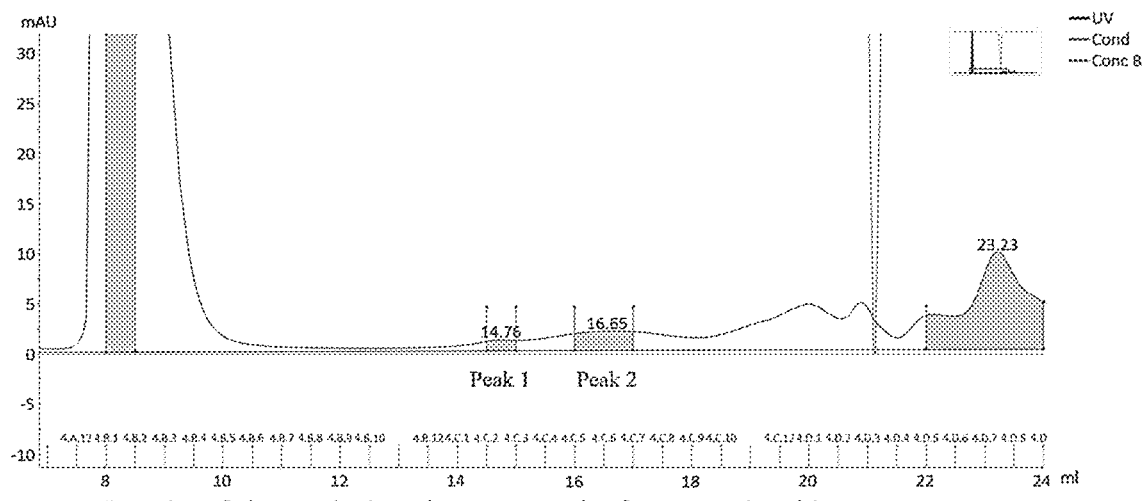
FIG. 11 shows size exclusion chromatograms for a urea-free control group and soaking treatment with 8 M urea in Example 4.
Figure 11:
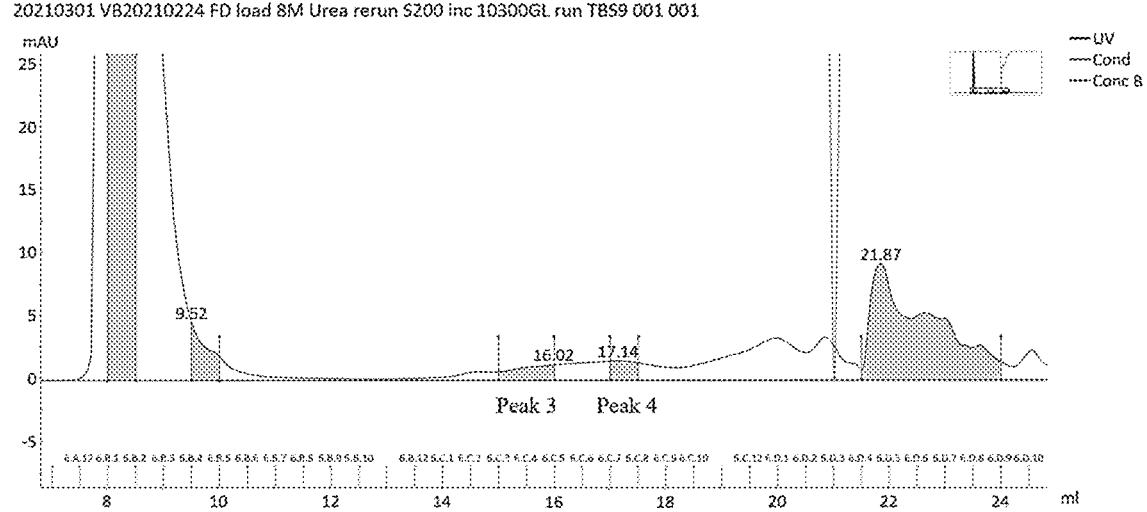
Figure 11:
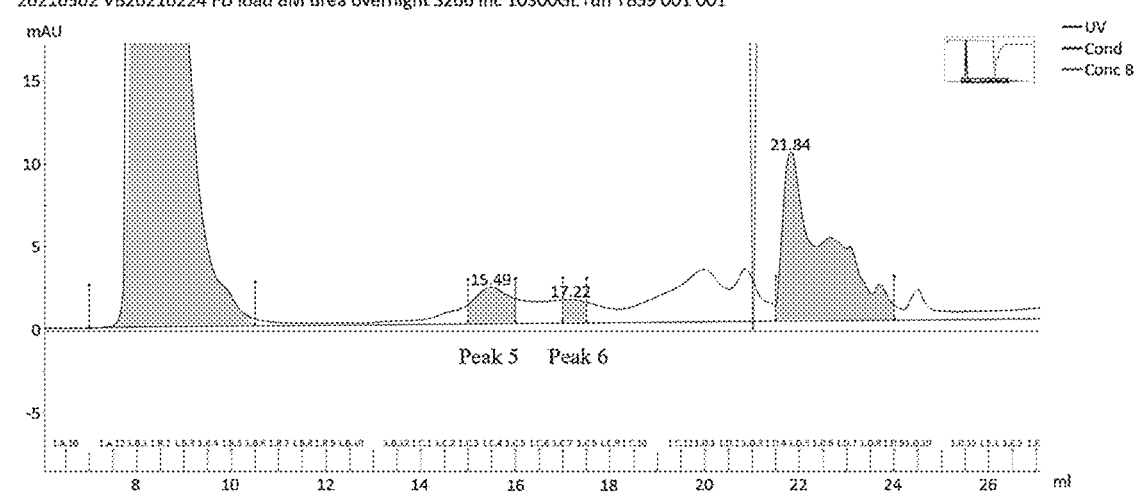
Figure 12:
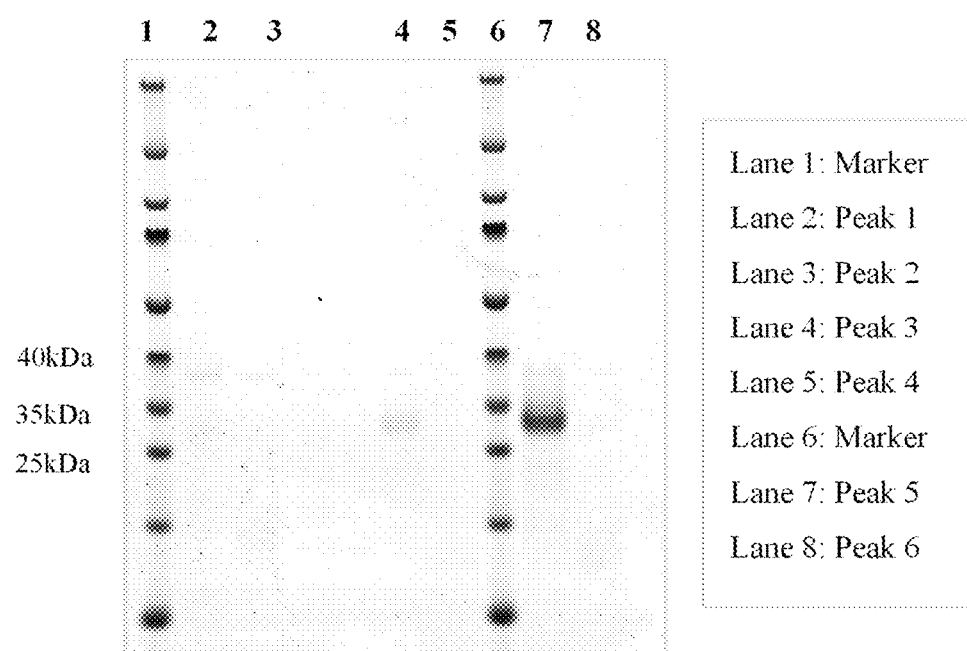
FIG. 12 shows SDS-PAGE detection results of size exclusion elution peaks of a urea-free control group and after treatment with 8 M urea in Example 4.

Results and Analysis:

As can be seen from FIG. 11, after the high-concentration urea treatment for three different durations, other substances with a molecular weight smaller than that of the main peak of the recombinant particle protein (peaks 1-5) could be separated in the size exclusion, and the peak formation times were basically the same. As can be seen from FIG. 12, only peak 5 (soaked in 8 M urea for 16 h) showed a distinct band between 25-35 kDa, while peak 3 (soaked in 8 M urea for 1 h) showed a lighter band between 25-35 kDa. No visible bands were found for peaks 1 and 2 without urea soaking. The experiment indicates that soaking in 8 M high-concentration urea helped to remove some small molecule impurities, with the preferred soaking time being more than 12 h.

2. Sodium chloride treatment (1) Four sodium chloride concentration investigation points, namely 50 mM, 100 mM, 150 mM, and 200 mM, were set up to observe the effect of sodium chloride at different concentrations on impurity removal: The experimental samples were the same as those used in the urea experiment. On the basis of 8 M urea addition, sodium chloride was further added to treat the samples. Four sodium chloride concentration investigation points, namely 50 mM, 100 mM, 150 mM, and 200 mM, were set up.

Figure 13:
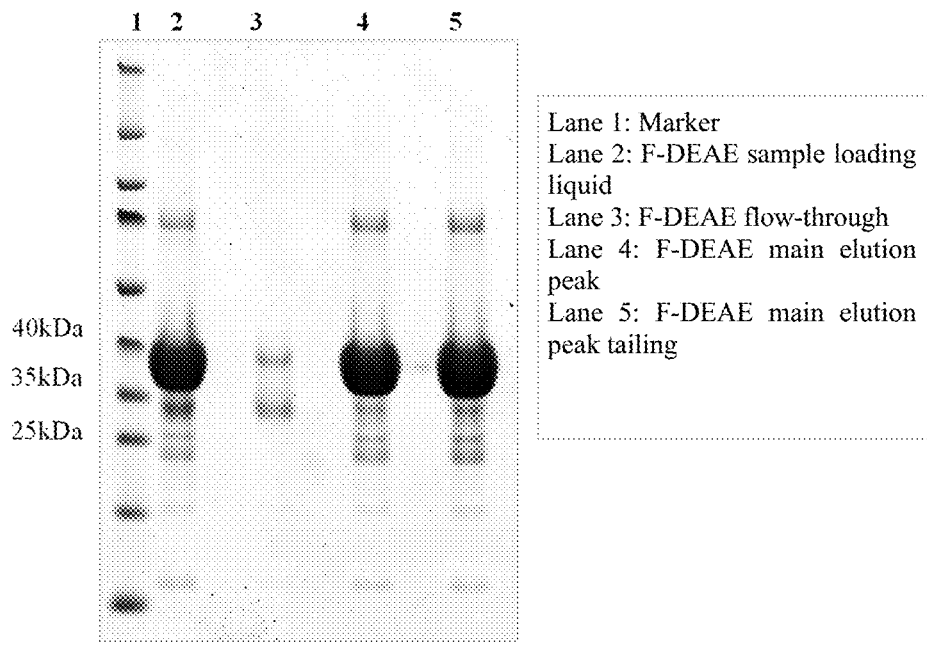
FIG. 13 shows an SDS-PAGE analysis of chromatographic peaks after treatment with four concentrations of sodium chloride in Example 4.
Figure 13:
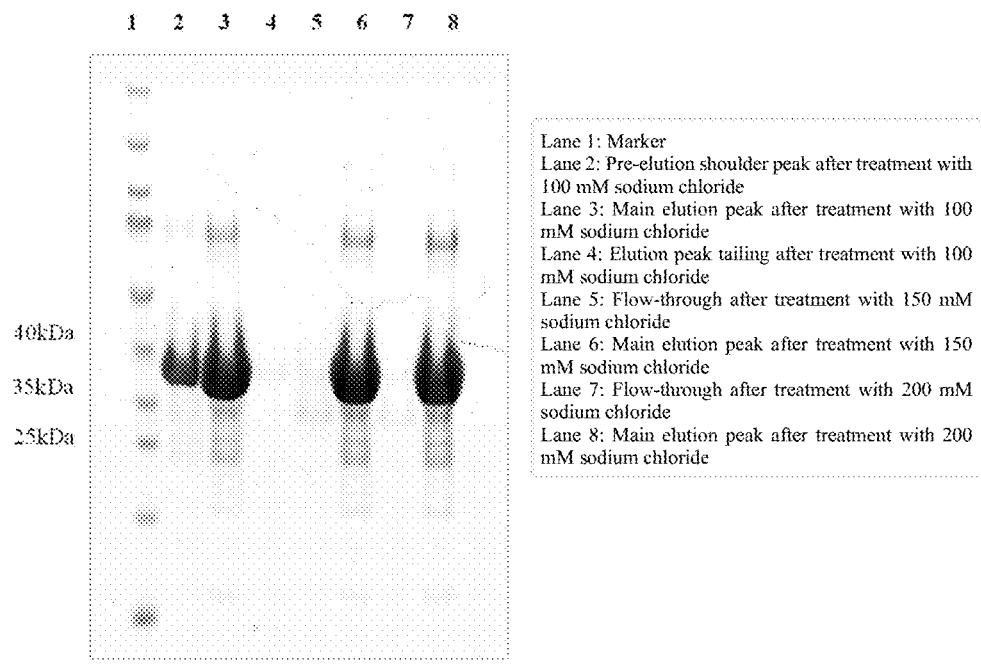

The recombinant particle protein samples were soaked for 16 h in 8 M urea and sodium chloride at four concentrations of 50 mM, 100 mM, 150 mM, and 200 mM. Subsequently, the samples were subjected to chromatographic purification using Fractogel® DEAE M packing, and their flow-through and elution peak fractions were subjected to SDS-PAGE detection (as shown in FIG. 13).

Results and Analysis:

As can be observed from FIG. 13a, after soaking in 8 M urea and 50 mM sodium chloride for 16 h, the content of the 25-35 kDa substance in the main elution peak was significantly reduced, and this substance appeared in the chromatographic loading flow-through. As can be observed from FIG. 13b, increasing the concentration of sodium chloride did not result in a significant reduction of the 25-35 kDa band compared to the treatment with 50 mM sodium chloride.

a) The pretreatment step of soaking the recombinant particle protein in 8 M high-concentration urea helped to remove the unidentified 25-35 kDa substance.

b) Adding sodium chloride on the basis of 8 M urea for soaking also helped to remove this unidentified substance, and the impurity removal effect of 50-200 mM sodium chloride showed no significant difference.

In summary, the preferred process conditions for pretreatment of the recombinant particle protein sample prior to Fractogel® DEAE M chromatography were soaking in 8 M urea and 50-200 mM sodium chloride.

(2) Verification experiment:

A comparison experiment with different salts (the salts selected to be compared included potassium chloride, sodium sulfate, and magnesium chloride; the salts for parallel comparison included potassium chloride, sodium sulfate, and magnesium chloride) was set up to observe the effects of different types and concentrations of salts on impurity removal:

① Experimental procedures:

A bacterial cell lysate supernatant was taken, adjusted to pH 9, then heated at 80° C. for 1 h, and centrifuged at 12000 g and 4° C. for 30 min to collect a supernatant. An equal volume of a pH 7.4 buffer containing 100 mM Tris-HCl, 5 mM EDTA, and 4% Triton® X-100 was added to the resulting supernatant, and 10% of the total volume of 1 M Tris-HCl pH 7.4 buffer was added. The mixture was heated at 60° C. for 10 min and immediately centrifuged at 6000 g for 10 min, and the supernatant was removed. The pellet was redissolved in a pH 9 buffer containing 20 mM Tris-HCl and 5 mM EDTA.

In order to explore and confirm the effects of commonly used salts, three salts with different valences and different acid radicals, namely KCl, $Na_2SO_4$, and $MgCl_2$, were selected. Based on the experience from the NaCl treatment experiments, 6 groups, namely 50 mM KCl, 100 mM KCl, 50 mM $Na_2SO_4$, 100 mM $Na_2SO_4$, 50 mM $MgCl_2$, and 100 mM $MgCl_2$, were set up. After overnight (16-18 h) soaking treatment, chromatographic purification was performed using Fractogel® DEAE M packing. During purification, the NaCl in the chromatography equilibration buffer was replaced with the corresponding salt for each group. After the chromatography was completed, the flow-through substances and elution peaks of each group were subjected to SDS-PAGE analysis.

② Experimental results:

a. Experimental results of treatment of the recombinant particle protein of the present application with KCl FIG. 14 (a) shows an SDS-PAGE gel image of samples treated with KCl after F-DEAE chromatography. It can be seen from the figure that no 25-35 kDa impurities appeared in the flow-through of the groups treated with two different concentrations of KCl; in the elution, due to the relatively low concentration, the impurity bands were not distinct, but the distribution of 25-35 kDa impurities was still visible; compared to the effect of soaking treatment with NaCl, KCl had no significant advantage.

b. Experimental results of treatment of the recombinant particle protein of the present application with $Na_2SO_4$ FIG. 14(b) shows an SDS-PAGE analysis image of samples treated with $Na_2SO_4$ after F-DEAE chromatography. It can be observed that after treatment with two different concentrations of $Na_2SO_4$ and subsequent F-DEAE chromatography, the recombinant particle protein product of the present application appeared in the flow-through, while there was no recombinant particle protein product of the present application in the elution. The chromatography also suggests that the UV absorption values during elution were extremely low. This indicates that the addition of $Na_2SO_4$ increased the ionization of the samples, so that the recombinant particle protein of the present application could not bind to the F-DEAE column. Therefore, $Na_2SO_4$ cannot be used as a salt for pretreating samples.

c. Experimental results of treatment of the recombinant particle protein of the present application with $MgCl_2$ During the treatment of the recombinant particle protein of the present application with $MgCl_2$, it was found that after the addition of 50 mM or 100 mM $MgCl_2$, the pH value of the buffer decreased from 8.9 to about 8.2 or 8.0, which was below the pH range specified for the F-DEAE chromatography process. If NaOH is used to adjust the pH back, poorly soluble $Mg(OH)_2$ precipitates tend to be produced. Therefore, $MgCl_2$ cannot be used as a salt for pretreating samples.

③ Experimental analysis

Through the comparison experiment with four salts—NaCl, KCl, $Na_2SO_4$, and $MgCl_2$—it was found that the flow-through after pretreatment with KCl contained fewer target impurities, but had no significant advantage compared to NaCl; $Na_2SO_4$, due to its high ionic strength, could cause the recombinant particle protein of the present application to flow through in the chromatography process; $MgCl_2$ could result in a decrease in the system's pH, and it was not advisable to adjust the pH back with NaOH.

Taking all factors into consideration, NaCl is the most suitable salt for pretreatment in terms of impurity removal effect, process compatibility, pH stability, etc.

Example 5. Two-Step Chromatographic Purification Process for Recombinant Particle Protein Product The recombinant particle protein sample solution pretreated sequentially in Example 3 and Example 4 was refined using ion exchange chromatography and hydrophobic chromatography. The first-step chromatographic purification was performed using the Fractogel® DEAE M chromatography process. The specific procedures and parameters are shown in Table 4. The collected Fractogel® DEAE M elution sample was first diluted in a buffer, and then 50% (w/v) sucrose stabilizer was added to prevent pelleting of the recombinant particle protein during the next chromatography step. The specific parameters are shown in Table 5. Then, the sample was further refined using a hydrophobic chromatography process with Octyl Bestarose 4FF (second-step chromatographic purification). The specific procedures and parameters are shown in Table 6.

1. Method for first-step chromatography: chromatography packing-Fractogel® DEAE M, retention time-12.5 min

TABLE 4

| Method for first-step chromatography | | |
|---|---|---|
| Chromatography procedures | Chromatography buffer/condition | Parameter |
| Equilibration buffer | 20 mM Tris-HCl, 5 mM EDTA, 8M Urea, 50 mM NaCl, pH 9.0 | 6 CV |
| pH after equilibration | 8.8 ± 0.05 | 8.80 |
| Rinse buffer 1 | 20 mM Tris-HCl, 5 mM EDTA, 8M Urea, 50 mM NaCl, pH 9.0 | 1.5 CV |
| Rinse buffer 2 | 20 mM Tris-HCl, 5 mM EDTA, 8M Urea, 2% Triton® X-100, pH 9.0 | 5 CV |
| Rinse buffer 3 | 20 mM Tris-HCl, 8M Urea, pH 9.0 | 5 CV |
| Rinse buffer 4 | 20 mM Tris-HCl, 4M Urea, pH 9.0 | 5 CV |
| Elution buffer | 20 mM Tris-HCl, 4M Urea, 150 mM NaCl, pH 9.0 | 2 CV |
| Collection range | 50 mAU-50 mAU | Optical path length of 2 mm |

TABLE 5

| Method for sample dilution before second-step chromatography | | |
|---|---|---|
| Procedures | Buffer for dilution | Dilution volume |
| Collected elution fraction from first-step chromatography | N/A | N/A |
| Buffer dilution | 20 mM Tris-HCl, 1M NaCl, 50% (w/v) sucrose, pH 9.0 | 2 × the volume of elution |
| Buffer dilution | 20 mM Tris-HCl, 2M NaCl, pH 9.0 | 1 × the volume of elution |

2. Method for second-step chromatography: chromatography packing-Octyl Bestarose 4FF, retention time-12.5 min

TABLE 6

Method for second-step chromatography

| Chromatography procedures | Chromatography buffer/condition | Parameter |
|---|---|---|
| Equilibration buffer | 20 mM Tris-HCl, 1M NaCl, 25% (w/v) sucrose, pH 9.0 | 2 CV |
| Rinsing buffer | 20 mM Tris-HCl, 1M NaCl, 25% (w/v) sucrose, pH 9.0 | 1.5 CV |
| Elution buffer | 20 mM Tris-HCl, 25% (w/v) sucrose, pH 9.0 | 3 CV |
| Collection range | 50 mAU-50 mAU | Optical path length of 2 mm |

Results and Analysis:

Through purity testing, it was found that after further refining through the above chromatography medium combination, the purity of the resulting product could reach more than 99.0%.

Example 6. Protective Effects of Different Concentrations and Types of Stabilizers on Recombinant Particle Protein Product During the intervals of different chromatography steps, pelleting and aggregation of recombinant particle proteins due to higher concentrations were observed, and the pelleting phenomenon showed an increasing trend with rising temperatures. It was necessary to add a stabilizer to improve protein stability and process robustness. In order to explore the influence of the concentration and type of the added stabilizer on the protective effect of the recombinant particle protein, three stabilizers, namely sucrose, sorbitol, and trehalose, were selected in this experiment. According to the process requirements and the conventional experience, the protective effects of the stabilizers at the concentrations shown in Table 7 below on the recombinant particle protein were investigated. The elution from Fractogel® DEAE M was taken, and the sample, stabilizer and buffer were mixed according to the volumes and sequence shown in Table 8. Additionally, a negative control group in which the stabilizer was replaced with purified water was set up. The mixed sample was incubated at 30° C. for 30 min, and the absorbance values at UV 320 nm and UV 280 nm after incubation were measured and recorded. The higher the absorbance value at UV 320 nm, the greater the extent of protein aggregation and pelleting. The specific results are shown in Table 9.

Results and Analysis:

As can be seen from Table 9, sucrose, sorbitol, and trehalose, at concentrations of 20% or greater, could prevent the pelleting in the recombinant particle protein solution after heating at 30° C. for 30 min, and the effects of the three are relatively similar.

It can be seen that after Fractogel® DEAE M chromatography, using sucrose, sorbitol or trehalose at a concentration of 20% or greater as a stabilizer could provide effective protection for the recombinant particle protein. Due to the indoor temperature control range of 18-26° C. in the laboratory and production workshop, the addition of the stabilizer can provide sufficient protein stability and process robustness assurance.

TABLE 7

Types of stabilizers and their investigated concentrations

| Stabilizer | Investigated concentration |
|---|---|
| Sucrose | 5%, 10%, 15%, 20%, 25% |
| Sorbitol | 5%, 10%, 15%, 20%, 25%, 30% |
| Trehalose | 2%, 4%, 6%, 8%, 10%, 15%, 20%, 25%, 30% |

TABLE 8

Dilution method for experimental stabilizer samples

| Sample/buffer | Volume of addition |
|---|---|
| Fractogel ® DEAE M elution | 200 μL |
| Stabilizer at 2 × investigated concentration | 400 μL |
| 4M NaCl 60 mM Tris-HCl pH 9.0 | 200 μL |

TABLE 9

Absorbance after incubation at 30° C. with different stabilizers at different concentrations

| Sample name | UV320 nm | UV280 nm |
|---|---|---|
| Negative control | 4.2 | 5.88 |
| Sucrose 5% | 2.94 | 4.48 |
| Sucrose 10% | 1.13 | 2.4 |
| Sucrose 15% | 0.24 | 1.26 |
| Sucrose 20% | 0.02 | 1.08 |
| Sucrose 25% | 0.03 | 1.04 |
| Sorbitol 5% | 3.66 | 5.33 |
| Sorbitol 10% | 1.92 | 3.39 |
| Sorbitol 15% | 0.24 | 1.35 |
| Sorbitol 20% | 0.04 | 1.06 |
| Sorbitol 25% | 0.04 | 1.07 |
| Sorbitol 30% | 0.04 | 1.05 |
| Trehalose 2% | 4.61 | 6.41 |
| Trehalose 4% | 3.59 | 5.08 |
| Trehalose 6% | 4.45 | 6.43 |
| Trehalose 8% | 2.7 | 4.21 |
| Trehalose 10% | 2.62 | 4.18 |
| Trehalose 15% | 1.81 | 3.23 |
| Trehalose 20% | 0.1 | 1.2 |
| Trehalose 25% | 0.11 | 1.16 |

In summary, the above examples and drawings are only for the purpose of illustrating preferred examples of the present invention, and are not intended to limit the protection scope of the present invention. Any modifications, equivalent substitutions, improvements, and the like made without departing from the spirit and principle of the present invention shall fall in the protection scope of the present invention.

SEQUENCE LISTING

Sequence total quantity: 1
SEQ ID NO: 1          moltype = AA  length = 309
FEATURE               Location/Qualifiers

```
source          1..309
                mol_type = protein
                organism = synthetic construct
SEQUENCE: 1
DSATHIKFSK RDEDGKELAG ATMELRDSSG KTISTWISDG QVKDFYLYPG KYTFVETAAP    60
DGYEVATAIT FTVNEQGQVT VNGKATKGDA HIGGSGGSGG SGGSMKMEEL FKKHKIVAVL   120
RANSVEEAKK KALAVFLGGV HLIEITFTVP DADTVIKELS FLKEMGAIIG AGTVTSVEQA   180
RKAVESGAEF IVSPHLDEEI SQFAKEKGVF YMPGVMTPTE LVKAMKLGHT ILKLFPGEVV   240
GPQFVKAMKG PFPNVKFVPT GGVNLDNVCE WFKAGVLAVG VGSALVKGTP VEVAEKAKAF   300
VEKIRGCTE                                                          309
```

What is claimed is:

1. A preparation method for a recombinant particle protein product, comprising the following steps:
   (1) transfecting a host cell with a plasmid vector comprising a sequence encoding the particle protein for expression in the cell;
   (2) harvesting and disrupting the host cell, and collecting a supernatant;
   (3) a. adjusting the pH of the supernatant to 9.0-10.0, and heating and incubating the supernatant at 80-100° C. for more than 15 min; then, after returning to room temperature, performing centrifugation, discarding a pellet, collecting a supernatant, and adding a dilution buffer to adjust the pH value to 7.0-8.0; and
   b. heating and incubating the solution at 50-65° C. for 5-20 min; performing centrifugation, discarding a supernatant, and collecting a pellet; resuspending the pellet in a resuspension buffer at pH 9.0-11.0; and
   (4) performing chromatographic purification;
   wherein the amino acid sequence of the recombinant particle protein product is set forth in SEQ ID NO: 1.

2. The preparation method according to claim 1, wherein after resuspending the pellet in step (3), urea and sodium chloride are added, followed by step (4).

3. The preparation method according to claim 2, wherein the urea is at a concentration of 6-8 M.

4. The preparation method according to claim 1, wherein in step (3)a, the dilution buffer comprises Tris-hydrochloric acid, acetic acid-sodium acetate, citric acid, or phosphoric acid.

5. The preparation method according to claim 1, wherein in step (3)b, the resuspension buffer comprises Tris-hydrochloric acid, acetic acid-sodium acetate, citric acid, or phosphoric acid.

6. The preparation method according to claim 5, wherein in step (3)b, the resuspension buffer further comprises ethylenediaminetetraacetic acid.

7. The preparation method according to claim 1, wherein in step (4), the chromatographic purification comprises both an anion exchange chromatography step and a hydrophobic chromatography step.

8. The preparation method according to claim 7, wherein a stabilizer is added to a collected elution fraction obtained from the anion exchange chromatography and to a buffer in the hydrophobic chromatography.

9. The preparation method according to claim 8, wherein the stabilizer is at a concentration of more than 20% (w/v).

10. The preparation method according to claim 8, wherein the stabilizer is selected from an amino acid, a polyol, or a saccharide.

11. The preparation method according to claim 10, wherein the amino acid is selected from arginine, glycine, or histidine.

12. The preparation method according to claim 10, wherein the polyol is selected from glycerol or sorbitol.

13. The preparation method according to claim 10, wherein the saccharide is selected from sucrose or trehalose.

14. The preparation method according to claim 7, wherein a medium for the hydrophobic chromatography step is Octyl Bestarose 4FF.

15. The preparation method according to claim 1, wherein step (3)a comprises adjusting the pH of the supernatant to 9.0-10.0, and heating and incubating the supernatant at 80-95° C. for 15-80 min.

16. The preparation method according to claim 1, wherein step (3)a comprises adjusting the pH of the supernatant to 9.0, and heating and incubating the supernatant at 80-90° C. for 15-80 min.

17. The preparation method according to claim 1, wherein step (3)b comprises heating and incubating the solution at 50-60° C. for 5-10 min.

* * * * *